US011895993B2

(12) United States Patent
Hosokawa et al.

(10) Patent No.: US 11,895,993 B2
(45) Date of Patent: Feb. 13, 2024

(54) METHOD OF PRODUCING A NOVEL ANIMAL MODEL FOR TAUOPATHIES

(71) Applicant: Tokyo Metropolitan Institute of Medical Science, Tokyo (JP)

(72) Inventors: Masato Hosokawa, Tokyo (JP); Hiroshi Shitara, Tokyo (JP); Masato Hasegawa, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 775 days.

(21) Appl. No.: 16/805,203

(22) Filed: Feb. 28, 2020

(65) Prior Publication Data

US 2020/0288682 A1 Sep. 17, 2020

(30) Foreign Application Priority Data

Mar. 1, 2019 (JP) ................................. 2019-037753
Feb. 27, 2020 (JP) ................................. 2020-032038

(51) Int. Cl.
| | |
|---|---|
| *A01K 67/027* | (2006.01) |
| *C07K 14/47* | (2006.01) |
| *C12N 5/10* | (2006.01) |
| *G01N 33/68* | (2006.01) |
| *C12N 15/01* | (2006.01) |

(52) U.S. Cl.
CPC ............ *A01K 67/027* (2013.01); *C07K 14/47* (2013.01); *C12N 5/10* (2013.01); *C12N 15/01* (2013.01); *G01N 33/68* (2013.01); *A01K 2207/15* (2013.01)

(58) Field of Classification Search
CPC .............. A01K 67/027; A01K 2207/15; A01K 2267/0318; A01K 67/0275; C07K 14/4711
See application file for complete search history.

(56) References Cited

PUBLICATIONS

Yoshida (2002, Biochemistry, 41:152203-15211).*
Hanes (2009, Journal of Neurochemistry, 1078:1167-1176).*
Hernandez, frontiers in Aging Neuroscience, 2020, 12:11, 6 pages.*
Saijo, 2020, Acta Neuropathologica, 139:63-77.*
Hosokawa, Masato, "Research Report (Exhibit 1)", Collection of Research Reports, Jul. 1, 2018, vol. 22, No. submitted Nov. 20, 2017, Publisher: Mitsui Sumitomo Insurance Welfare Foundation.
"Back Numbesr of Publication of Grant Results from Jul. 2013 to Jul. 2021 (Exhibit 2)", https://www.ms-ins.com/welfare/document/backnumber.htm, Publisher: Homepage of Mitsui Sumitomo Insurance Welfare Foundation, retrieved Oct. 4, 2022.
"List of Research Reports FY 2018 (Exhibit 3)", https://www.ms-ins.com/welfare/document/list/list2016.htm, Publisher: Mitsui Sumitomo Insurance Welfare Foundation, Published in: retrieved Oct. 4, 2022.
"Front and Back Covers of vol. 22 of the Collection of Research Reports (Exhibit 4)", Collection of Research Reports, Jul. 1, 2018, vol. 22, Publisher: Mitsui Sumitomo Insurance Welfare Foundation.
Clavaguera F, et al. Transmission and spreading of tauopathy in transgenic mouse brain. Nat Cell Biol. 2009;11(7):909-913. doi:10.1038/ncb1901.
Iba, Michiyo et al. "Synthetic tau fibrils mediate transmission of neurofibrillary tangles in a transgenic mouse model of Alzheimer's-like tauopathy." The Journal of neuroscience : the official journal of the Society for Neuroscience vol. 33,3 (2013): 1024-37. doi:10.1523/JNEUROSCI.2642-12.2013.
Clavaguera, Florence et al. "Brain homogenates from human tauopathies induce tau inclusions in mouse brain." Proceedings of the National Academy of Sciences of the United States of America vol. 110,23 (2013): 9535-40. doi:10.1073/pnas.1301175110.
Lasagna-Reeves, Cristian A et al. "Alzheimer brain-derived tau oligomers propagate pathology from endogenous tau." Scientific reports vol. 2 (2012): 700. doi:10.1038/srep00700.
Lasagna-Reeves, Cristian A et al. "Tau oligomers impair memory and induce synaptic and mitochondrial dysfunction in wild-type mice." Molecular neurodegeneration vol. 6 39. Jun. 6, 2011, doi:10.1186/1750-1326-6-39.
Takuma, et al. Isoforms changes of tau protein during development in various species, Developmental Brain Research, vol. 142, Issue 2, 2003, pp. 121-127, doi.org/10.1016/S0165-3806(03)00056-7.
Grover, A et al. "5' splice site mutations in tau associated with the inherited dementia FTDP-17 affect a stem-loop structure that regulates alternative splicing of exon 10." The Journal of biological chemistry vol. 274,21 (1999): 15134-43. doi:10.1074/jbc.274.21.15134.
D'Souza, Ian, and Gerard D Schellenberg. "tau Exon 10 expression involves a bipartite intron 10 regulatory sequence and weak 5' and 3' splice sites." The Journal of biological chemistry vol. 277,29 (2002): 26587-99. doi:10.1074/jbc.M203794200.
Taniguchi-Watanabe, Sayuri et al. "Biochemical classification of tauopathies by immunoblot, protein sequence and mass spectrometric analyses of sarkosyl-insoluble and trypsin-resistant tau." Acta neuropathologica vol. 131,2 (2016): 267-280. doi:10.1007/s00401-015-1503-3.

(Continued)

*Primary Examiner* — Valarie E Bertoglio
(74) *Attorney, Agent, or Firm* — Suzannah K. Sundby, Esq.; Canady + Lortz LLP

(57) ABSTRACT

The present invention provides a disease model animal for tauopathies which reproduces the expression pattern of tau protein isoforms of adult human brain, that is, approximately equal amounts of 3R type tau and 4R type tau being expressed in the adult brain. The method for producing the disease model animal for tauopathies of the present invention comprises the steps of: preparing a tau seeds; and injecting the tau seeds in the brain of an animal carrying a mutation in the tau gene which fails to express the tenth exon. The animal carrying a mutation in the tau gene which fails to express the tenth exon may be produced by using any of the genome editing, gene targeting or base editing technologies.

8 Claims, 25 Drawing Sheets

Specification includes a Sequence Listing.

(56) References Cited

PUBLICATIONS

Goedert, Michel. "Tau filaments in neurodegenerative diseases." FEBS letters vol. 592, 14 (2018): 2383-2391. doi:10.1002/1873-3468.13108.

Guo, Jing L et al. "Unique pathological tau conformers from Alzheimer's brains transmit tau pathology in nontransgenic mice." The Journal of experimental medicine vol. 213,12 (2016): 2635-2654. doi:10.1084/jem.20160833.

Sharma, Govinda et al. "Tau isoform expression and phosphorylation in marmoset brains." The Journal of biological chemistry vol. 294,30 (2019): 11433-11444. doi:10.1074/jbc.RA119.008415.

Nishida, Keiji et al. "Targeted nucleotide editing using hybrid prokaryotic and vertebrate adaptive immune systems." Science (New York, N.Y.) vol. 353,6305 (2016): aaf8729. doi:10.1126/science.aaf8729.

Hasegawa, M et al. "Alzheimer-like changes in microtubule-associated protein Tau induced by sulfated glycosaminoglycans. Inhibition of microtubule binding, stimulation of phosphorylation, and filament assembly depend on the degree of sulfation." The Journal of biological chemistry vol. 272,52 (1997): 33118-24. doi:10.1074/jbc.272.52.33118.

Hosokawa, Masato et al. "Progranulin reduction is associated with increased tau phosphorylation in P301L tau transgenic mice." Journal of neuropathology and experimental neurology vol. 74,2 (2015): 158-65. doi: 10.1097/NEN.0000000000000158.

Hwang, Woong Y et al. "Efficient genome editing in zebrafish using a CRISPR-Cas system." Nature biotechnology vol. 31,3 (2013): 227-9. doi:10.1038/nbt.2501.

Mali, Prashant et al. "RNA-guided human genome engineering via Cas9." Science (New York, N.Y.) vol. 339,6121 (2013): 823-6. doi:10.1126/science.1232033.

Wang, Haoyi et al. "One-step generation of mice carrying mutations in multiple genes by CRISPR/Cas-mediated genome engineering." Cell vol. 153,4 (2013): 910-8. doi:10.1016/j.cell.2013.04.025.

Yang, Hui et al. "One-step generation of mice carrying reporter and conditional alleles by CRISPR/Cas-mediated genome engineering." Cell vol. 154,6 (2013): 1370-9. doi:10.1016/j.cell.2013.08.022.

Larkin, M A et al. "Clustal W and Clustal X version 2.0." Bioinformatics (Oxford, England) vol. 23,21 (2007): 2947-8. doi:10.1093/bioinformatics/btm404.

* cited by examiner

FIG. 3

```
Wild_mTAU    GTGCAGATAATTAATAAGAAGCTGGATCTTAGCAACGTCCAGTCCAAGTGTGGCTCGAAG    60
mTAU_13      GTGCAGATAATTAATAAGAAGCTGGATCTTAGCAACGTCCAGTCCAAGTGTGGCTCGAAG    60
mTAU_2       GTGCAGATAATTAATAAGAAGCTGGATCTTAGCAACGTCCAGTCCAAGTGTGGCTCGAAG    60
             ************************************************************

Wild_mTAU    GATAATATCAAACACG--------------------------------------------    76
mTAU_13      GATAATATCAAACACGGGACGTAAATTACGGGTGACTAATCCGATATATACACGCAAACG   120
mTAU_2       GATAAT------------------------------------------------------    66
             ******

Wild_mTAU    ------------------------------------------------------------
mTAU_13      GAGCCTCAATATTTATTATTTGCTTATTCCTTCATGTCGGACGAGGCTTATATTATGGAT   180
mTAU_2       ------------------------------------------------------------

Wild_mTAU    ------------------------------------------------------------
mTAU_13      CATATACATTTATAGAAACCTGAAACATTGGAGTACTTCTACTGTTCGCAGTCATAGCCA   240
mTAU_2       ------------------------------------------------------------

Wild_mTAU    --------------------------------------------TCCCGGGTGGAGG     94
mTAU_13      CAGCATTTATAGGCTACGTCCTTCCATGAGGACAAATATCATTCTGA-----GGTGGAGG   295
mTAU_2       ------------------------------------------------------------

Wild_mTAU    CAGTGTGAGTACTGTCGCAGTCTCCATGAGGTGTGCTGCAGCCTTTGCTGTAACAAGTGT   154
mTAU_13      CAGTGTGAGTACTGTCGCAGTCTCCATGAGGTGTGCTGCAGCCTTTGCTGTAACAAGTGT   355
mTAU_2       ------------------------------------------------------------

Wild_mTAU    CATGAGTGTGTCCTTGTGAGACATTGCATAGAATAAATCATCTAGGGCTCAGGACCTCCT   214
mTAU_13      CATGAGTGTGTCCTTGTGAGACATTGCATAGAATAAATCATCTAGGGCTCAGGACCTCCT   415
mTAU_2       ----------------------------TGCATAGAATAAATCATCTAGGGCTCAGGACCTCCT   102
                                         ********************************

Wild_mTAU    GTGTCCCC   217
mTAU_13      GTGTCCCC   423
mTAU_2       GTGTCCCC   110
             ********
```

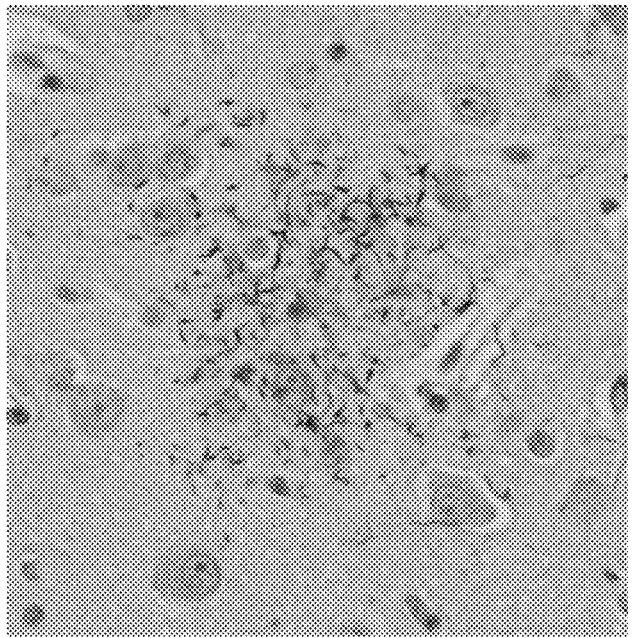
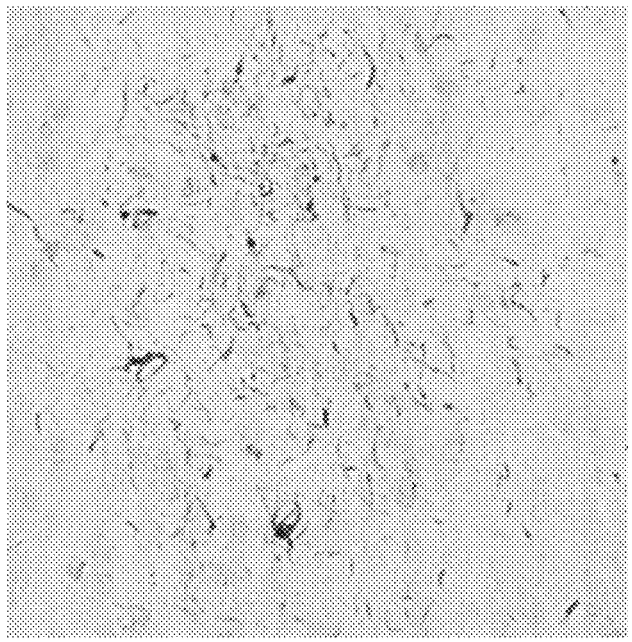
FIG. 16

METHOD OF PRODUCING A NOVEL ANIMAL MODEL FOR TAUOPATHIES

CROSS REFERENCE TO RELATED APPLICATIONS

This application claims priority to the following Japanese Patent Applications: No. 2019-037753, filed Mar. 1, 2019; and No. 2020-032038, filed Feb. 27, 2020, the entire disclosure of these applications are hereby expressly incorporated by reference into this application.

REFERENCE TO A SEQUENCE LISTING SUBMITTED VIA EFS-WEB

The content of the ASCII text file of the sequence listing named "20200228_150001_001US1_seq" which is 5.08 kb in size was created on Feb. 27, 2020 and electronically submitted via EFS-Web herewith the application is incorporated herein by reference in its entirety.

TECHNICAL FIELD

This application relates to a method of producing a novel disease model animal for tauopathies and to the novel disease model animal produced by the method thereof. Specifically, this application relates to a method for producing disease model animal for sporadic tauopathies, comprising the steps of providing a tau seeds, and injecting the tau seeds into an animal brain; and the novel disease model animal for tauopathies produced by the method thereof.

BACKGROUND OF THE INVENTION

A member of microtubule associated protein, tau, is involved in promotion of polymerization and stabilization of microtubules in neuronal cells. Brain of a patient with Alzheimer's disease (AD) has pathological tau fibrils associated with characteristic neuronal degeneration such as neurofibrillary tangle (NFT), neuropil thread (NT) and others. Tau, a water-soluble protein, may be fibrotic and deposited in the neuronal cells as the major constituent component of the pathological tau fibrils, which may remain in situ as extra-cellular NFT, even after the neuronal cells were dead. The tau fibrils in both inside and outside of neuronal cells are hereafter referred to as "pathological tau fibrils". In addition to AD, the pathological tau fibrils are deposited in the brain of a patient with several well-known neurodegenerative diseases, including Pick's disease (PiD), corticobasal degeneration (CBD), progressive supranuclear palsy (PSP), senile dementia of the NFT type (SD-NFT), argyrophilic grain disease (AGD) and others. These neurodegenerative diseases are collectively referred to as tauopathies, meaning "diseases in which tau is deposited". In AD, distribution of the pathological tau fibrils changes as the disease advances. The pathological tau fibrils show a specific pattern of onset: initial emergence in the caerulean nucleus; then, in the entorhinal cortex and hippocampus; and, finally, spreading all over the cerebral cortex. As the distribution of the pathological tau fibrils correlates with the clinical symptoms, it is predicted that the formation of the pathological tau fibrils is the direct factor to cause the neuronal degeneration.

Although it is assumed that normal tau protein in an aqueous solution has random coil configuration, the tau protein deposited in the patient's brain forms amyloid fibrils rich in cross beta structure. A tau fibril further aggregates monomer tau proteins. It is therefore expected that a structural change of aqueous monomers into water-insoluble fibrils should be closely involved in the pathological onset of the neurodegenerative diseases. Nonetheless, the underlying mechanism has not been elucidated. It has neither been elucidated why the distribution in the brain of pathological tau fibrils changes over time. At present, only therapy available for the tauopathies is supportive care. Thus, a novel therapy for the tauopathies should be developed by understanding the mechanisms how the pathological tau fibrils are deposited by the conformation change of the tau protein and how the distribution in the brain of the pathological tau fibrils changes over time.

Most of the tauopathies including AD are sporadic, although there exist familial (hereditary) tauopathies. It is thus necessary to develop a disease model animal which reflects the human clinical conditions more precisely by reproducing the phenomenon that the distribution of the pathological tau fibrils changes over time in the brains of the animals expressing the same tau protein species in the same amounts as expressed in the normal human individuals.

There have been several reports on experimental model systems so far that insoluble tau were injected as seed into a specific site of mouse brain and the pathological tau fibrils were deposited in the brains. Among these reports, Clavaguera et al. (Non-Patent documents 1 and 3) and Iba et al. (Non-Patent document 2) injected insoluble tau into brain of a transgenic mouse which express wild-type or mutant human tau protein. Namely, a transgenic mouse was produced which constitutively express in the neurons wild-type or mutant tau protein by driving their coding DNAs with promotor region of either neuron-specific murine Thy 1 gene (Non-Patent documents 1 and 3) or murine prion protein gene (Non-Patent document 2). Either a brain cell lysate of the transgenic mouse (Non-Patent document 1), tau seeds prepared by adding heparin to myc-tag fused recombinant human mutant tau protein (Non-patent Reference 2) or brain extracts of a human patient with tauopathy (Non-Patent document 3), respectively, were injected into a brain of the above-mentioned transgenic mouse. In Non-Patent document 4, tau oligomers or tau seeds derived from a brain of a human AD patient was injected into brains of wild-type mice. In Non-Patent document 5, brain of a wild-type mouse was injected with either tau oligomers prepared by supplementing beta 42 amyloid oligomers with human wild-type recombinant tau protein or tau seeds prepared by shaking the tau oligomers.

In Non-Patent document 1, pathological tau fibrils were detected by Gallyas-Braak silver staining in the transgenic mice six (6), twelve (12) and fifteen (15) months after injection. The localization in the brain of the pathological tau fibrils were observed to change over time. In Non-Patent document 1, no change of localization in the brain of the pathological tau fibrils were observed in experiments in which the insoluble tau was injected not to transgenic mouse but to wild-type mouse. In Non-Patent document 2, the pathological tau fibrils were detected as early as one (1) month after injection. Note that the pathological tau fibrils were detected in the transgenic mouse at eight (8) to nine (9) months old without injecting the insoluble tau. In Non-Patent document 3, the pathological tau fibrils were detected six (6) months after injecting brain extracts of a human patient with a tauopathy into the wild-type mouse brain. In Non-Patent document 4, the pathological tau fibrils were detected eleven (11) months after injecting the tau oligomers derived from a brain of a patient with AD into a wild-type mouse brain. In Non-Patent document 5, cognitive function declined thirty (30) hours after injection in one cohort of wild-type mice whose brains were injected with beta 42 amyloid oligomer, while cognitive function was not affected in another cohort whose brains were injected with tau seeds. In any of these cohorts, neither the decline of the cognitive function nor deposition of the pathological tau fibrils several months after injection was examined.

One of the problems in using mouse as a disease model animal is that isoforms of tau protein expressed in adult brain are different between a human and a mouse. FIG. 1 is a schematic representation of all of the various isoforms of tau protein, possibly generated by the alternative splicing, expressed in the adult brain of primates and mammals (FIG. 1). Genes coding human and non-human animal tau proteins are highly homologous, sharing a common exon/intron structure. Both human and non-human animal tau proteins have isoform polymorphism generated by the alternative splicing of the second and third exons in the amino-terminal region and the tenth exon in the carboxyl-terminal region. The longest variant is the full-length isoform comprising the amino acid sequence encoded in all the exons including the second, third and tenth exons. The shortest variant is the isoform which comprises none of the second, third and tenth exons. As for the amino-terminal region, in addition to the isoform which comprises both the second and the third exons, there are two more isoforms: one which comprises the second exon but not the third exon; and the other which comprises neither the second nor the third exon. As for the carboxyl-terminal region, there are two isoforms: one which comprises the tenth exon; and the other which does not comprise the tenth exon. Because the alternative splicing in the amino-terminal region and the carboxy-terminal region occurs independently, there exist six isoforms in total, as shown in FIG. 1. Tau protein has four repeat sequences in the microtubule-binding domain. The tenth exon corresponds to the second repeat sequence from the amino-terminal end. The variant polypeptide without the tenth exon is referred to as 3R type, because it has three repeat sequences in the microtubule-binding domain. On the other hand, the variant polypeptide with the tenth exon is referred to as 4R type, because it has four repeat sequences in the microtubule-binding domain. The pathogenesis of tauopathies involves conformation change to convert water-soluble tau protein into insoluble fibrils. It is considered that, the more repeat sequences the microtubule-binding domain has, the conformation change is more likely to occur. Of the polymorphic isoforms of the tau protein, 3R and 4R types attract more attention.

In human, only 3R type tau is expressed in the fetal brain, while approximately identical amounts of 3R type tau and 4R type tau are expressed in the adult brain. In mouse, on the other hand, only 3R type tau is expressed in the brain until neonatal period and then only 4R type tau is expressed in the brain after weaning period (Non-Patent document 6). This difference is believed to arise from the difference of stem-loop structure between the tenth exon and the tenth intron (Non-Patent documents 7 and 8). It is considered that the conformation change of tau protein to convert from water-soluble monomer to insoluble fibrils is more likely to occur in 4R type tau than in 3R type tau, because 4R type tau has one more repeat sequence in the microtubule-binding domain than 3R type tau.

It has been known that each of the tauopathy diseases has distinct isoform composition of tau protein in the pathological tau fibrils deposited in the brain of human tauopathy patients. Namely, it has been known that equal amounts of 3R and 4R type tau are deposited in the brain of an AD patients, only 3R type tau is deposited in a PiD patients, and only 4R type tau is deposited in the brain of CBD and PSP patients (e.g. Non-Patent document 9). Equal amounts of 3R and 4R type tau are known to be deposited in the brain of a patient with SD-NFT, a tauopathy, as well as in the brain of a patient with many neurological diseases including Down syndrome. It has also been known that only 4R type tau is deposited in the brain of a patient of tauopathies such as AGD, Globular glial tauopathy and Tau astrogliopathy, and many neurological diseases including Huntington disease (Non-Patent document 10). Further, as for the hereditary familial frontotemporal lobar degeneration with parkinsonism caused by a mutant in tau (MAPT) gene, it has been known that either equal amounts of 3R and 4R type tau, or 3R type tau alone or 4R type tau alone is deposited in the brain, depending on the specific amino acid mutation involved (Non-Patent document 10).

In contrast to these human clinical reports, no experimental injection of insoluble fraction derived from the brain of an AD patient has been reported to induce the deposition of 3R type tau, although 4R type tau was successfully deposited (Non-Patent documents 3 and 11). Injection of insoluble fraction derived from the brain of a patient with Pick disease has failed to induce deposition of 3R type tau. Thus, the conventional experimental model systems of tauopathy do not deem to reproduce the expression pattern of tau protein isoforms in the adult human brain, in which approximately equal amounts of 3R and 4R tau types are expressed. Not only mouse but also rat and marmoset, which are likely to be used as disease model animal for tauopathy, express only 3R type tau in the brain until newborn stage, and then only 4R type tau after weaning (Non-Patent documents 6 and 12).

Therefore, there is an abundant need for an experimental system which reproduces the isoform expression pattern of tau protein in adult human brain, where approximately equal amounts of 3R tau and 4R type tau are expressed.

PRIOR ART LITERATURE

Non-Patent Documents

Non-patent document 1: Clavaguera, F. et al., Nat. Cell Biol., 11: 909 (2009)
Non-patent document 2: Iba, M. et al., J. Neurosci., 33: 1024 (2013)
Non-patent document 3: Clavaguera, F. et al., Proc. Natl. Acad. Sci. U.S.A., 110: 9535 (2013)
Non-patent document 4: Lasagna-Reeves, C. A. et al., Sci. Rep., 2: 700 (2012)
Non-patent document 5: Lasagna-Reeves, C. A. et al., Mol. Neurodegener., 6: 39 (2011)
Non-patent document 6: Takuma, H. et al., Developmental Brain Res., 142: 121 (2003)
Non-patent document 7: Grover, A. et al., J. Biological. Chem., 274: 15134 (1999)
Non-patent document 8: D'Souza, I. and Schellenberg G. D., J. Biological. Chem. 277: 26587 (2002)
Non-patent document 9: Taniguchi-Watanabe, S. et al., Acta Neuropathol., 131: 267 (2016)
Non-patent document 10: Goedert, M., FEBS Letters, 592: 2383 (2018)
Non-patent document 11: Guo, J. L. et al., J. Exp. Med. 213: 2635 (2016)
Non-patent document 12: Sharma, G., et al., J. Biological. Chem., 294: 11433 (2019)

SUMMARY OF THE INVENTION

Problem to be Solved by the Invention

As explained in the above, the problem to be solved by the present invention is to develop a disease model animal for sporadic tauopaties which reproduces the expression pattern in the adult human brain of repeat sequence isoforms in the microtubule-binding domain of tau protein, in that approximately equal amounts of 3R tau and 4R tau are expressed.

The present invention provides a method for producing a disease model animal for sporadic tauopathies. The method of the present invention comprises the steps of: preparing tau seeds; and injecting the tau seeds in the brain of an animal carrying a mutation in the tau gene which fails to express the tenth exon.

In the method for producing a disease model animal for sporadic tauopathies of the present invention, the animal carrying a mutation in the tau gene which fails to express the tenth exon can be any animal species, but may be a mouse, a rat or a marmoset.

In the method for producing a disease model animal for sporadic tauopathies of the present invention, the tau seeds may be derived from a brain of a human patient with a tauopathy.

In the method for producing a disease model animal for sporadic tauopathies of the present invention, the tau seeds may comprise a sarkosyl insoluble fraction derived from the brains of the human patient with the tauopathy.

In the method for producing a disease model animal for sporadic tauopathies of the present invention, the animal carrying a mutation in the tau gene which fails to express the tenth exon may be produced by using any of the genome editing, gene targeting or base editing technologies.

The present invention provides a disease model animal for sporadic tauopathies. The disease model animal for sporadic tauopathies of the present invention is produced by the method for producing a disease model animal for sporadic tauopathies of the present invention.

The disease model animal for sporadic tauopathies of the present invention may have a polynucleotide consisting of a nucleotide sequence as set forth in SEQ ID NO: 1 or 2 on its chromosome. Here, SEQ ID NO: 1 is a nucleotide sequence on the tenth exon region of Tau 3R/4R #2, one mutant strain of mouse carrying a mutation in the tau gene which fails to express the tenth exon, and SEQ ID NO: 2 is a nucleotide sequence on the tenth exon region of Tau 3R/4R #13, another mutant strain of mouse carrying a mutation in the tau gene which fails to express the tenth exon.

The present invention provides an animal brain which is dissected from the disease model animal for sporadic tauopathies of the present invention.

The present invention provides a method for analyzing the disease model animal for sporadic tauopathies of the present invention. The method for analyzing the disease model animal for sporadic tauopathies of the present invention comprises the steps of: dissecting the brain from at least some of the animals to whom the tau seeds are injected; and characterizing the pathological tau fibrils in the brain.

In the method for analyzing a disease model animal for sporadic tauopathies of the present invention, the animal carrying a mutation in the tau gene which fails to express the tenth exon can be any animal species, but may be a mouse, a rat or a marmoset.

In the method for analyzing a disease model animal for sporadic tauopathies of the present invention, the animal carrying a mutation in the tau gene which fails to express the tenth exon may be produced by using any of the genome editing, gene targeting or base editing technologies.

In the method for analyzing a disease model animal for sporadic tauopathies of the present invention, the pathological tau fibrils in the brains may be characterized by at least one property of the group consisting of the isoform composition of tau protein comprised in the pathological tau fibrils, the phosphorylation state of the tau protein, and Gallyas-Braak silver stainability of brain tissues comprising the pathological tau fibrils.

The present invention provides a method for analyzing the disease model animal for sporadic tauopathies of the present invention. The method for analyzing the disease model animal for sporadic tauopathies of the present invention comprises steps of: monitoring the behavior of the disease model animal for sporadic tauopathies in a test environment; monitoring the behavior of a control animal in the test environment; and comparing the behavior of the disease model animal for sporadic tauopathies with the behavior of the control animal.

The present invention provides a method for screening a substance which affects the pathological tau fibrils in the brain of a disease model animal for sporadic tauopathies. The method for screening a substance of the present invention comprises of the steps of: providing tau seeds; injecting the tau seeds in the brain of a test group of animals carrying a mutation in the tau gene which fails to express the tenth exon; administering a test substance to the animals of the test group; injecting the tau seeds in the brain of a control group of animals carrying a mutation in the tau gene which fails to express the tenth exon; dissecting the brains from at least some animals of both test and control groups; charactering the pathological tau fibrils in the brains of the both test and control groups; and comparing the characteristics of the pathological tau fibrils in the brains of the test group with the characteristics of the pathological tau fibrils in the brains of the control group.

In the method for screening a substance which affects the pathological tau fibrils in the brain of a disease model animal for sporadic tauopathies of the present invention, the pathological tau fibrils in the brains may be characterized by at least one property of the group consisting of the isoform composition of tau protein comprised in the pathological tau fibrils, the phosphorylation state of the tau protein, Gallyas-Braak silver stainability of brain tissues comprising the pathological tau fibrils.

In the method for screening a substance which affects the pathological tau fibrils in the brain of a disease model animal for sporadic tauopathies of the present invention, the tau seeds may be derived from a brain of a human patient with a tauopathy.

In the method for screening a substance which affects the pathological tau fibrils in the brain of a disease model animal for sporadic tauopathies of the present invention, the tau seeds may comprise a sarkosyl insoluble fraction derived from a brain of a human patient with tauopathy.

In the method for screening a substance which affects the pathological tau fibrils in the brain of a disease model animal for sporadic tauopathies of the present invention, the animal carrying a mutation in the tau gene which fails to express the tenth exon may be produced by using any of the genome editing, gene targeting or base editing technologies.

In the method for screening a substance which affects the pathological tau fibrils in the brain of a disease model animal for sporadic tauopathies of the present invention, the animal carrying a mutation in the tau gene which fails to express the tenth exon may have a polynucleotide consisting of a nucleotide sequence as set forth in SEQ ID NO: 1 or 2 on its chromosome. SEQ ID NO: 1 is a nucleotide sequence on the tenth exon region of Tau 3R/4R #2, one mutant strain of mouse carrying a mutation in the tau gene which fails to express the tenth exon, and SEQ ID NO: 2 is a nucleotide sequence on the tenth exon region of Tau 3R/4R #13, another mutant strain of mouse carrying a mutation in the tau gene which fails to express the tenth exon.

In the method for screening a substance which affects the pathological tau fibrils in the brain of a disease model animal for sporadic tauopathies of the present invention, the animal carrying a mutation in the tau gene which fails to express the tenth exon can be any animal species, but may be a mouse, a rat or a marmoset.

In the method for screening a substance which affects the pathological tau fibrils in the brain of a disease model animal for sporadic tauopathies of the present invention, the pathological tau fibrils in the brains may be characterized by change of the localization over time of the pathological tau fibrils in the brain.

BRIEF DESCRIPTION OF DRAWINGS

FIG. 3 is a sequence alignment, prepared by Clustal X, of chromosomal DNA in the region from the tenth exon to the tenth intron of tau gene comparing Tau 3R/4R #2 and #13, mutant strains of mouse carrying mutations in the tau gene which fails to express the tenth exon, with wild-type C57BL/6J strain.

In FIG. 9, the upper left panel shows a fluorescent microscopic photograph observed under the condition which only detects the fluorescent dye labeled for the antibody specific for the 3R type tau (RD3); the upper right panel shows a fluorescent microscopic photograph observed under the condition which only detects the fluorescent dye labeled for the antibody specific for the 4R type tau (anti-4R); the lower left panel shows an image prepared by merging the upper left and upper right panels (merged).

FIG. 16 (left) is microscopic photographs of tissue specimens of right cerebral cortex of the Tau 3R/4R mutant mouse brains prepared by injecting tau seeds derived from human brains of patients with CBD, in which 4R type tau is deposited, into the Tau 3R/4R mutant mouse brains; dissecting the mutant mouse brains eight months after injection; fixing the mutant mouse brains in 4% paraformaldehyde; sectioning; and staining the tissue specimens immunohistochemically with an antibody against phosphorylated tau (AT8). FIG. 16 (right) is a microscopic photograph of typical astrocytic plaques observed in the brain of human patient with CBD. The astrocytic plaques similar to those of FIG. 16 (left) was detected in the cerebral cortex of the mutant mouse brains.

FIG. 17 (right) is an immunoblot result obtained by preparing sarcosyl insoluble fractions from human brain of the patients with Alzheimer's Disease (AD), progressive supranuclear palsy (PSP), corticobasal degeneration (CBD) and Pick's disease (Pick); separating proteins in the sarcosyl insoluble fractions by electrophoresis; transferring the separated proteins to a membrane; and staining the membrane with an antibody against phosphorylated tau (AT8).

DETAILED DESCRIPTION OF THE INVENTION

Figure 1:
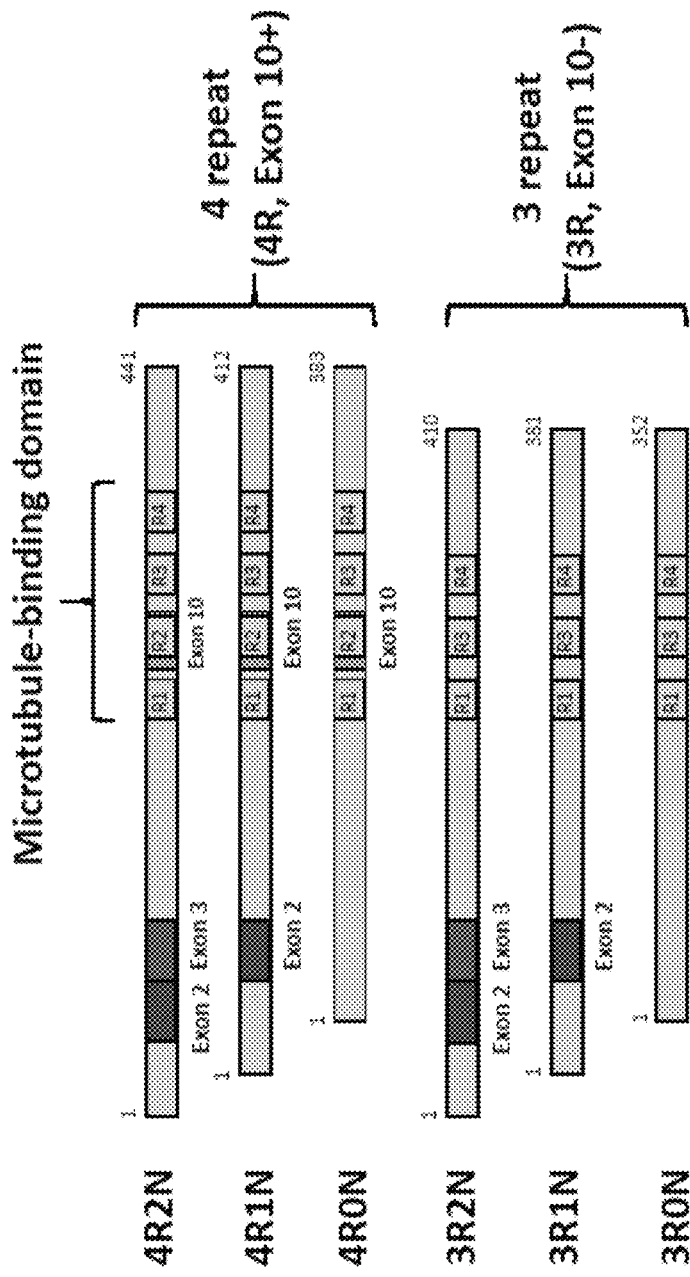
FIG. 1 is a schematic representation of all the isoforms of tau protein which may be generated by the alternative splicing in the brain of primates and mammals.

Unless stated otherwise, words in the singular include the plural. That is, the singular forms "a," "an," and "the" may include the plural reference. For example, "a gene" may refer to one or more genes. Similarly, "a patient" or "the patient" may refer to one or more patients.

In the present specification, a disease model animal for sporadic tauopathies is defined as a disease model animal which reproduces a phenomenon that distribution of pathological tau fibrils changes over time in the brain of a patient with a sporadic tauopathy, which accounts for the majority of patients with tauopathies. The animal used for the disease model animal for sporadic tauopathies of the present invention is an animal carrying a mutation in the tau gene which fails to express the tenth exon. In the present specification, an "animal only carrying normal tau genes" refers to an animal only carrying endogenous tau genes, comprising of any foreign tau gene which can neither be expressed in the brain nor which is derived from any species other than that of the animal species. Therefore, the "animal only carrying normal tau genes" of the present invention may carry a foreign gene for the gene other than the tau gene. In addition, the "animal only carrying normal tau genes" of the present invention may carry a foreign tau gene as long as the foreign tau gene cannot be expressed in the brain. Here, a foreign gene is defined as a DNA introduced into a germline cell of the animal through a route which is comprised of, but not limited to, DNA injection into a fertilized egg and an embryonic cell; transfection into an ES cell; infection of a viral vector to an animal egg or embryo; and others. A foreign tau gene refers to a foreign gene comprising a DNA which encodes at least a part of a tau protein derived from any species of organism. A gene which "can be expressed in the brain" refers to the gene being operably linked to a DNA which has a function for the transcriptional and/or translational control (for example, promotor and/or enhancer), so that the gene product, RNA or protein, encoded in the gene is produced in the brain.

An animal which only carries normal tau genes is capable of expressing both 3R and 4R types tau by alternative splicing of the tenth exon of the tau gene. Approximately equal amounts of 3R and 4R type taus are expressed in the adult brain of the human, while only 4R type tau is expressed in the adult brain of mouse and others. Thus, it would be possible to express 3R type in the adult brain, if the expression of the tenth exon of the tau gene is suppressed without depending on the alternative splicing. One of the solutions is to produce a transgenic animal carrying stably in its germline an engineered tau gene which fails to express the tenth exon. In the present specification, an engineered tau gene which fails to express the tenth exon is defined as a mutant of tau gene which does never express the tenth exon, while all the other exons may be expressed normally, so that the 3R type isoform of tau protein is produced which is identical to the one generated by the alternative splicing. An example of the engineered tau gene which fails to express the tenth exon may be generated by introducing a mutation in which the tenth exon is excised together with the adjacent introns to generate an aberrant splicing in which the ninth exon is directly linked to the eleventh exon. Another example may be generated by introducing a nonsense or frameshift mutation which arrests the translation at the carboxyl terminal region of the tenth exon or a missense mutation causing substitution or deletion of an amino acid residue(s), so that the isoform comprising the tenth exon is absent, or cannot maintain the structure and function of a normal tau protein.

Accordingly, in the present specification, an animal carrying an engineered tau gene which fails to express the tenth exon expresses only 3R type isoform tau, at least in the adult brain. Especially in an animal species which expresses only 4R type isoform tau when the animal carries only normal tau genes, when the animal carries an engineered tau gene which fails to express the tenth exon, an individual which carries the engineered gene but not any normal tau gene (hereafter referred to as "homo" individual) expresses only 3R type isoform in the adult brain, while an individual which carries both the engineered gene and the normal tau gene (hereafter referred to as "hemi" individual) expresses both 3R and 4R type tau isoforms in the adult brain. In the animal species which expresses only 4R type tau isoform in the brain when the animal carries only normal tau genes, the hemi individual shows the tau isoform pattern identical to that of the human, that is, the tau isoform pattern in which both 3R and 4R type tau are expressed in the adult brain. By using the hemi individuals, therefore, it is possible to provide a disease model animal for tauopathies which is closer to the human pathology.

In the present specification, it is preferable that the animal species of the animal carrying engineered tau gene which fail to express the tenth exon is an animal species which expresses only 4R type tau isoform in the adult brain, when the animal carries only normal tau genes. Any animal species may serve as a disease model animal for tauopathies, however, it is preferable to employ an animal species which has already been used as an laboratory animal in the field of neurosciences. As the tauopathy diseases decline cognitive and behavioral functions, it is further preferable to use an animal species which has higher brain functions. Here it is noted that the phylogenetic or systematic relationship alone cannot necessarily explain whether the adult brain expresses only 4R type tau isoform, or both 3R and 4R type tau isoforms. Because it is believed to be due to the difference of the stemloop structure in the region from the tenth exon to the tenth intron (Grover, A., et al., J. Biological. Chem., 274: 15134 (1999); D'Souza, I. and Schellenberg, G. D., J. Biological. Chem. 277: 26587 (2002)). For example, in the rodents, the mice and the rats express only 4R type tau isoform in the adult brain, while the rabbits express both 3R and 4R type tau isoforms. The marmosets, which belong to the primates as the humans do, show the same expression pattern as the mice and rats in that only 4R type tau isoform is expressed in the adult bran (Sharma, G., et al., J. Biological. Chem., 294: 11433 (2019)).

An animal carrying an engineered tau gene which fails to express the tenth exon is produced by the genome editing methods, gene targeting methods or base editing methods. Here, the genome editing methods refer to genetic engineering technologies in which any given position of the genome sequence can be deleted, substituted, and/or inserted with the Double Strand Breaks or DSBs by using the complex comprising a nuclease such as CRISPR-Cas9 (clustered regularly interspaced short palindromic repeats/CRISPR associated proteins) system, ZFN (Zinc-Finger Nuclease) system, TALEN (Transcription Activator-Like Effector Nuclease) system and others (Doudna, J. and Mali, P. ed., CRISPR-Cas: A Laboratory Manual, CSHL Press, 2016). The gene targeting methods refer to genetic engineering technologies in which an endogenous gene is engineered by using the homologous recombination (Behringer, R. et al., Manipulating the Mouse Embryo: A Laboratory Manual, 4th ed., CSHL Press, 2014). The latter methods may be employed for deleting a gene, deleting an exon, introducing a gene, introducing a point mutation, and others. The base edition methods refer to genetic engineering technologies in which a C-G base pair in a DNA is converted to a T-A base pair without Double Strand Breaks by linking a cytidine deaminase to a RNA programmable catalytically inactivated Cas 9 complex (Nishida, K., et al., Science, 353: aaf8729 (2016)).

The tau seeds of the present specification refer to substances which are capable of depositing the pathological tau fibrils and which include insoluble substances derived from the pathological tau fibrils in the human brain of a patient with a tauopathy or the pathological tau fibrils in the brain of non-human animal with a tauopathy; and insoluble or soluble complex of tau protein other than the pathological tau fibrils. The tau seeds of the present specification can deposit the pathological tau fibrils by injection in the brain of laboratory animals as well as cultured cells in vitro (WO2013/073219). The above-mentioned complex of tau protein includes tau complex obtained by incubating in vitro a tau monomer and non-protein substance such as sulfated glycosaminoglycan including, for example, dextran sulfate and pentosan polysulfate (Hasegawa, M., et al., J. Biol. Chem., 272:33118 (1997); Japanese published unexamined application No. 2015-122979). The tau monomer includes a monomer of tau protein derived from the human and others; a monomer of tau protein prepared in vitro by the recombinant DNA technologies or a complex with the monomer; and a monomer of tau protein obtained as a degradation product of the pathological tau fibrils formed by cells cultured in vitro or a complex with the monomer. The tau seeds include any substance comprising the tau protein as a monomer, an oligomer, their complex and other forms, as long as the substance is able to form pathological tau fibrils in the cells cultured in vitro or in the brain of an animal.

In the present specification, preparation, formation or deposition of the tau seeds may be evaluated biochemically by an immunoblotting analysis of fractions which are insoluble in detergent-free buffer and which are not still soluble following supplementation with a certain detergent (such as sarkosyl) so that the precipitates are separated by centrifugation, or alternatively, by an immunoblotting analysis of fractions which are insoluble following a sequential fractionation in which a fraction insoluble in a detergent is sequentially treated with another detergent with higher solubilizing ability (for example, fractionation with triton X-100 followed by sarkosyl (Hosokawa, M. et al., J. N. Neuropath. Exp. Neurol., 74: 158 (2015)). The sequential fractionation is carried out by solubilizing the tau seeds in more than one detergents with different solubilizing ability in the order starting from the detergent with the lower solubilizing ability. Sarkosyl is the detergent with the highest solubilization ability in the detergents used for the differential solubilization. It is also evaluated biophysically by a direct observation with an electron microscope or an atomic force microscope, as well as by determine the degree of formation of beta sheet structure with the fluorophotometry using a fluorescent dye, such as thioflavine T (ThT) or thioflavine S (ThS), or the circular dichromism. The tau seeds prepared in vitro by reacting a monomer of tau protein with sulfated glycosaminoglycan may be characterized by a property comprising, but not limited to, the sarcosyl insolubility, fluorescence by the fluorescent dyes, electron microscopic morphology of the fibrils, results of circular dichromism analysis. The sarkosyl insoluble fractions derived from a patient with tauopathy, for example, is prepared as follows. Frozen brain sample dissected from a tauopathy patient (between 0.2 g and 0.5 g) is homogenized in five times volume of a buffer such as A68 buffer (10 mM Tris-HCl (pH 7.5), 0.8 M NaCl, 1 mM EGTA, 1 mM DTT) to make a suspension. Sodium N-lauroyl sarcosinate is added to the suspension to the final concentration of 1%, followed by a 30 minutes incubation at 37° C. The suspension is centrifuged (for example, at 12,000×g, for 10 minutes, at 25° C.) and a supernatant is collected. The supernatant is apportioned into about 1300 microliter aliquots in Eppendorf type tubes and further centrifuged (for example, at 100,000×g, for 20 minutes, at 25° C.), then the supernatants are discarded, a precipitate is collected. The insoluble fractions are suspended in 90 microliter of a buffer such as 30 mM Tris-HCl (pH 7.5) per the starting material of the frozen brain sample between 0.2 g and 0.5 g, and are stored frozen, to be injected, without further dilution, into the brain of the animal carrying the engineered tau gene which fails to express the tenth exon.

When the tau seeds are injected into the brain of the animal, the site of injection includes, but not limited to, the mesencephalic substantia nigra, caerulean nucleus, entorhinal cortex, striatum and hippocampus. The analysis of the pathological tau fibrils with the biochemical and immunohistochemical methods is carried out with, but not limited to, female animals, and the analysis of brain functions with the behavior tests is carried out with, but not limited to male animals. Anesthetized animals are held to a brain stereotaxis apparatus and the tau seeds are injected into the brain. The site of injection may be determined according to: Franklin, K. B. J. and Paxinos, G. (The Mouse Brain in Stereotaxic Coordinates, 4th ed., 2012, Academic Press); Paxinos, G. and Watson, C. (The Rat Brain in Stereotaxic Coordinates, 7th ed., 2013, Academic Press); and Hardman, C. D. and Ashwell, K. W. S. (Streotaxic and Chemoarchitectural Atlas of the Brain of the Common Marmoset (*Callithrix jacchus*), 2012, CRC Press). For example, for the injection into the right striatum of mouse, the position is set to A-P: +0.2 mm, M-L: +2.0 mm and D-V: −2.6 mm. For the injection into the right mesencephalic substantia nigra, the position is set to A-P: −3.0 mm, M-L: −1.3 mm and D-V: −4.7 mm. 5 microliter of tau seeds suspension is injected with an instrument for microinjection such as 10 microliter Hamilton syringe. Rapid dissection of a brain from a mouse may be carried out by decapitation.

The precise mechanism has not been elucidated how the pathological tau fibrils in the brain are formed from the tau seeds injected into the brain. It is thought, however, that the tau seeds injected into the brain are incorporated into neuronal cells to serve as nuclei for aggregating monomers of tau protein expressed in the cells, forming characteristic intracellular pathological structures such as NFT, NT and others. Morphological features of the pathological structure may be detected by histological observation. Such morphological features include, but not limited to, individual shape of the pathological structures, their localization inside and outside the neuronal cells, and their tissue distribution in the brain. The immunohistochemical and biochemical features of the pathological structures may be detected by the reaction with antibodies including, but not limited to, an antibody against the tau protein, an antibody against 3R type tau protein, an antibody against 4R type tau protein, and an antibody specific to phosphorylated tau protein. In addition, the biochemical features of the pathological structures include, but not limited to, the detectability in the insoluble fractions and the presence or absence as well as the degree of posttranslational modification such as phosphorylation and others and these features may be detected by an immunoblotting analysis of fractions which are insoluble in detergent-free buffer and which are not still soluble following supplementation with a certain detergent (such as sarkosyl) so that the precipitates are separated by centrifugation, or alternatively, by an immunoblotting analysis of fractions which are insoluble following a sequential fractionation in which a fraction insoluble in a detergent is sequentially treated with another detergent with higher solubilizing ability (for example, fractionation with triton X-100 followed by sarkosyl (Hosokawa, M. et al., N. Neuropath. Exp. Neurol., 74: 158 (2015).

In the present specification, a "test cohort" refers to one or more animals treated under a condition in whose effect is to be confirmed. In the present specification, a "control cohort" refers to one or more animals treated under a condition which is different from the condition for the test cohort. The conditions for the test and control cohorts may differ in that, even though the injection surgery is performed for both the test and control cohorts, the injection solution is comprised of the tau seeds or not, that the injection solution is comprised of a substance which is distinct from the tau seeds in addition to the tau seeds, and/or that the tau seeds injected in the test cohort has a different characteristics from the tau seeds injected in the control cohort; or that a surgery to inject the tau seeds are performed for the test cohort but no surgery is performed at all for the control cohort. In the method for screening of the present invention, a "test substance" refers to each of candidate medicinal substances to be screened whose effect on the formation of the pathological tau fibrils is unknown. The test substance of the present invention may be injected together with the tau seeds, or administered through alternative route. The alternative route may include, but not limited to, oral administration, parenteral administration, inhalation, injection into an vein, a muscle, the peritoneal cavity and others. The administration of the test substance of the present invention may be performed once or more than once, continuously, or intermittently, before, at the same time and/or after a step of injecting the tau seeds into the brain. In the method for screening of the present invention, a "control substance" refers to a substance whose effect on the formation of the pathological tau fibrils has been known. The comparison of the features of the pathological tau fibrils is conducted, but not limited to, by comparing the features of the pathological tau fibrils in the brain of the animals dissected after the same period of time has passed since the surgery to inject into the brain was performed to the animals under different conditions, and/or by comparing the features of the pathological tau fibrils in the brain of the animals after different periods of time has passed since the surgery to inject into the brain was performed to the animals under the same conditions.

In the present specification, the features of the behavior of the animals include, but not limited to, features evaluated or determined by monitoring and recording the behavior of the animals under the test environment as shown in the following behavior tests. The behavior tests of mice may be conducted using the protocols described in, for example, Crawley, J. N. (What's Wrong With My Mouse?: Behavioral Phenotyping of Transgenic and Knockout Mice, 2nd ed., John Wiley & sons, (2007)). The behavior tests of rats may be conducted using the protocols described in, for example, Whishaw, I. Q. and Kolb, B. (The Behavior of the Laboratory Rat: A Handbook with Tests, Oxford University Press (2004)). The behavior tests of marmosets may be conducted using the protocols described in, for example, Watson, C. F. I. (Social Contagion in Common Marmosets (*Callithrix jacchus*): Implications for Cognition, Culture and Welfare, University of Stirling Ph. D. thesis, https://dspace.stir.ac.uk/handle/1893/3446#t1 (2011)) and Marini, R. P., et al. (The Common Marmoset in Captivity and Biomedical Research, 1st ed., Academic Press (2018)).

In the present specification, to "dissect brain from at least some of the animals" means that after conducting a surgery to inject into the brain under the same condition in a cohort of a plurality of animals, not all the animals of the cohort are sacrificed to dissect the brain after the same period of time has passed since the injection into the brain was performed, but some animals are spared to be sacrificed to dissect the brain after different period of time. For example, the animal of the same cohort may be sacrificed to dissect the brain three months or six months after injection into the brain.

The sequences as set forth in the Sequence Listings attached to the present specification are as follows.
SEQ ID NO: 1
DNA sequence of the tenth exon of Tau 3R/4R #2.
SEQ ID NO: 2
DNA sequence of the tenth exon of Tau 3R/4R #13.
SEQ ID NO: 3
DNA sequence of short guide RNA tau sgRNA candidate complementary sequence-6.
SEQ ID NO: 4
DNA sequence of forward primer for preparing tau sgRNA-6.
SEQ ID NO: 5
DNA sequence of reverse primer for preparing tau sgRNA-6.
SEQ ID NO: 6
SDNA sequence of forward primer for identifying genome edited animals.
SEQ ID NO: 7
DNA sequence of reverse primer for identifying genome edited animals.
SEQ ID NO: 8
DNA sequence of the tenth exon of the wild type C57BL/6.
SEQ ID NO: 9
DNA sequence encoding tracrRNA region of DNA fragment for synthesizing short guide RNA
tau sgRNA-6, derived from *Streptococcus pyogenes*.
SEQ ID NO: 10
Full-length RNA sequence of short guide RNA tau sgRNA-6.
SEQ ID NO: 11
DNA sequence of the donor DNA in which the sequence involved in the splicing of the tenth exon in the region between the tenth exon and the tenth intron of the mouse tau gene is replaced with the equivalent sequence of human tau gene.

All the references and documents mentioned or referred to in the present specification are incorporated by reference herein in their entirety.

Examples of the present invention described below are intended to be illustrative only, and not intended to limit the technical scope of the present invention. The technical scope of the present invention is limited only by the claims. Without departing from the spirit and scope of the present invention, various modifications of the present invention may be made for example, the addition, deletion, and replacement of features of the present invention.

Experiments described in the examples of the present specification were authorized by the ethical review committee on animal experimentation of Tokyo Metropolitan Institute of Medical Science as Animal Experimentation as Animal Experimentation Program Registry No. 13066, under the title "Construction of Model for Neurodegenerating Diseases Using Mice, Rats and Rabbits and Exploration of Treatments" on Mar. 29, 2013.

EXAMPLES

Example 1 Production of Animal Expressing an Engineered Tau Gene which Fails to Express the Tenth Exon (1.1) Materials and Methods
(1.1.1) Selection of the Short Guide RNA Employing methods well known by those skilled in the art, and considering various factors, a position for genome editing by CRISPER/Cas9 was selected from the mouse genome in the region of tau gene between the tenth exon and the tenth intron. As the result, DNA sequence of the short guide RNA tau sgRNA complementary sequence candidate-6 (5'-GAAGGAUAAUAUCAAACACGUCCCGG-3', SEQ ID NO: 3) was selected.

(1.1.2) Preparation of Cas 9 Messenger RNA and Short Guide RNA

Plasmid for Cas 9 (pCMVCas 9, Transposagen, INTEGRALE (formerly APRO Science Inc.)) was cut by a restriction enzyme Xba I (NEB # R0145S, New England Biolabs Japan Inc.) and the linearized DNA was purified with QIAquick PCR Purification Kit (QIAGEN #28104, QIAGEN Japan Inc.). The linearized DNA and mMESSAGE mMACHINE T7 Ultra Kit (Life Technologies # AM1345M, Life Technologies Japan, Ltd.) were used to synthesize Cas 9 mRNA. MEGAclear Kit (Life Technologies # AM1908, Life Technologies Japan, Ltd.) was used to purify the Cas 9 mRNA. The short guide RNA tau sgRNA-6 of the present invention is a single strand RNA in which the tau sg RNA complementary sequence-6, as selected in the previous section (1.1.1), was linked to the RNA in the region for binding Cas protein according to Hwang, W. Y. et al. (Nature Biotechnology, 31: 227 (2013)). In order to prepare template DNA for synthesizing the tau sgRNA-6 by transcription, a vector for synthesizing sgRNA was prepared in which a DNA fragment derived from *Streptococcus pyogenes* coding tracrRNA region at 3' terminal end of tau sgRNA-6 (SEQ ID NO: 9, 5'-GTTT-TAGAGCTAGAAATAGCAAGT-TAAAATAAGGCTAGTCCGTTATCAACTT-GAAAAAGT GGCACCGAGTCGGTGCTTTTAAA-3') was inserted to a vector (pTAKN-2). Using the vector as a template, PCR reaction was conducted with the forward primer for preparing the tau sgRNA-6 (5'-GACT-TAAGCTAATACGACTCACTATAGGATAATAT-CAAACACGTCCGTTTTAGAGCTAGAAATAGCAAGT-3', SEQ ID NO: 4), the reverse primer for preparing the tau sgRNA-6 (5'-AAAAGCACCGACTCGGTGCC-3', SEQ ID NO: 5) PrimeSTAR HS DNA Polymerase (TaKaRa Bio # R010A, Takara Bio Inc.) and QIAquick PCR Purification Kit (QIAGEN #28104, QIAGEN Japan Inc.). The PCR product was purified to be used as the template DNA fragment for synthesizing tau sgRNA-6. The template DNA fragment for synthesizing tau sgRNA-6 and MEGAshortscrip T7 Kit (Life Technologies # AM1354M, Life Technologies Japan, Ltd.) were used to synthesize the RNA. After the synthesis, the tau sgRNA-6 was purified with MEGAclear Kit (Life Technologies # AM1908, Life Technologies Japan, Ltd.).

(1.1.3) Microinjection of Cas 9 Messenger RNA and Short Guide RNA Tau sgRNA-6 and Manipulation of the Embryos Together with Cas 9 mRNA, tau sgRNA-6 was microinjected into pronuclear stage fertilized egg. The injected mouse embryos were transferred into uterus of pseudopregnant mice (Mali, P. et al., Science, 339: 823 (2013), Wang, H. et al., Cell, 153: 910 (2013), Yang, H. et al., Cell, 154: 1370 (2013)). In some experiments, pronuclear stage fertilized eggs of C57BL/6 strain received microinjection of tau sgRNA-6 and Cas 9 mRNA as well as circular DNA of a plasmid prepared by cloning the region between the tenth exon and the tenth intron of the mouse tau gene into a cut site for restriction enzyme Eco RV of pBluescript II SK (+), replacing a part of the inserted mouse sequence which is involved in the splicing of the tenth exon with an equivalent sequence of human tau gene to make a donor sequence (SEQ ID NO: 11). A silent mutation substituting the nucleotide 495 for thymidine was introduced in the donor sequence of SEQ ID NO: 11 so that a mouse could be recognized which incorporated into its chromosome the donor sequence substituted with the human tau gene by digesting the genome DNA with a restriction enzyme Tau I.

(1.1.4) Genotyping of Newborn Animals

A drop of blood from the tail of the mouse was collected on a filter paper, which was cut out in a round shape with 1.2 mm in diameter and used as a PCR template. The PCR reaction was carried out with a forward primer (5'-CCA-GATTCCTTTTGTGACTTCCAGGGTGCCATCC-3', SEQ ID NO: 6), a reverse primer (5'-CCAGAGATGAGG-GAAGAGGTGTCAGCC-3', SEQ ID NO: 7) and MightyAmp (Takara Bio Inc.) using an ABI Veriti thermal cycler (Applied Biosystems, Thermo Fisher Scientific K.K.) under the condition of initial incubation for 2 minutes at 98° C. followed by 32 cycles of incubating for 10 seconds at 98° C., for 15 seconds at 60° C., for 35 seconds at 68° C. in this order. The PCR reaction product was subjected to 1% agarose gel electrophoresis. The chromosome DNA sequence of tau gene between the tenth exon and the tenth intron of Tau 3R/4R mutant mouse was determined by cloning the corresponding band into pMD20-T (Takara Bio Inc.) and dye terminator sequencing. The chromosome DNA sequences of tau gene between the tenth exon and the tenth intron of a plurality of Tau 3R/4R mutant mouse strains and wild-type C57BL/6J strain were analyzed by sequence alignment using Clustal X described by Larkin, M. A. et al. (Bioinformatics, 23: 2947 (2007)).

(1.1.5) Immunoblotting

Mouse brain was homogenized in A68 buffer (10 mM Tris-HCl, pH 7.5, 0.8 M NaCl, 1 mM EDTA, 10% sucrose) and treated in an ultracentrifuge at 100,000×g, 4° C., for 20 minutes. The supernatant was stored at −20° C., and an aliquot was subjected to dephosphorylation reaction with alkaline phosphatase. Samples were suspended in the SDS-PAGE sample buffer and heated at 100° C. for 5 minutes. The electrophoresis was conducted on a 10% SDS-PAGE gel at 200 V for 45 minutes. After the electrophoresis, the proteins separated in the gel were transferred to a PVDF membrane. Following blocking with 3% gelatine, the transferred PVDF membrane was treated overnight with first antibodies: T46 (1:1,000, Invitrogen (Thermo Fisher Scientific K.K.)), RD3 (1:1,000, Millipore (Merck KGaA)), anti-4R (1:1,000, produced in the Inventors' laboratory), AT8 (1:1,000, Innogenetics (Cosmo Bio Co., Ltd)), pS396 (1:1000, Calbiochem, (Merck KGaA)) and an antibody specific to mouse tau (1:1,000, produced in the Inventors' laboratory). After rinsing, the PVDF membrane was reacted for one hour with anti mouse IgG-HRP or anti rabbit HRP (1:1,000, Bio-Rad (Bio-Rad Laboratories, Inc.)) and the chemiluminescence was generated using SuperSignal West Dura Extended Duration Substrate (Thermo Fisher Scientific K.K.). The chemiluminescence was detected with LAS-4000 mini (GE Healthcare Japan Corporation). After the chemiluminescence detection, the PVDF membrane was rinsed and reacted for one hour with anti-mouse IgG-Biotin or anti-rabbit IgG-Biotin (1:500, Vector Laboratories (Funakoshi Co., Ltd.)). The PVDF membrane was rinsed, immersed in ABC solution (Vector Laboratories (Funakoshi Co., Ltd.)) for one hour and subjected a chromogenic reaction with diaminobenzidine/$NiCl_2$/$H_2O_2$.

(1.1.6) Extraction of Sarkosyl Insoluble Fractions Derived from Brain of AD Patients Brain (0.2 g) of an AD patient was homogenized in 1.8 mL of A68 buffer. 1.8 mL of A68 buffer and 400 microliter of 20% sarkosyl were added and incubation was conducted at 37° C. for 30 minutes. After centrifugation at 10,000×g, 4° C., for 10 minutes, supernatant was collected and subjected to further centrifugation at 50,000 rpm, 4° C., for 20 minutes. The pellet was rinsed with saline, suspended in 30 microliter of 30 mM Tris-HCl (pH 7.5) and subjected to sonication (Grover, A. et al., J. Biological Chem., 274: 15134 (1999)). The sonicated pellet was suspended in a final volume of 90 microliter of 30 mM Tris-HCl (pH 7.5) per 0.2 g of the frozen brain sample, the starting material, and stored frozen. The sarkosyl insoluble fractions thus prepared were injected to the brain of the animals carrying an engineered tau gene which fails to express the tenth exon without further dilution. For tau seeds derived from a health control human used for control experiments, insoluble fractions were prepared similarly to those derived from the brain of AD patients and injected to the brain of the animals.

(1.1.7) Production of a Model for Propagation in the Brain of Pathological Tau Fibrils Using the Tau 3R/4R Mutant Mice The sarkosyl insoluble fractions derived from the AD patient brain as described in the above section (1.1.5) was injected to right striatum (Anterior-Posterior=+0.2 mm, Medial-Lateral=+2.0 mm, Dorsal-Ventral=−2.6 mm relative to the bregma) of the Tau 3R/4R mutant mice (5 microliter per head). The brain was dissected eight months after injection and fixed in 4% paraformaldehyde. Then, the fixative was replaced with 20% sucrose solution. The brain was sectioned at 30 micrometer and subjected to immunohistochemical staining. The thin sliced sections were treated in formic acid for ten minutes, subjected to an autoclave at 110° C. for ten minutes, followed by hydrogen peroxide treatment at room temperature for 30 minutes and reacted with biotinylated AT8 antibody (1:1,000, Innogenetics (Cosmo Bio Co., Ltd)). Then, the sections were reacted with avidin-biotinylated HRP complex (Vector Laboratories (Funakoshi Co., Ltd.)) and subjected a chromogenic reaction with diaminobenzidine/ammonium nickel sulfate. Counter staining was performed with Kernechtrot solution (Merck KGaA) (D'Souza, I. and Schellenberg G. D., J. Biological. Chem. 277: 26587 (2002)). For staining with antibodies specific to 3R type and 4R type tau isoforms, RD3 antibody (1:1,000, Millipore (Merck KGaA)) and anti-4R antibody (1:1,000, produced in the Inventors' laboratory) were used respectively, and Hematoxylin was used for counter staining. HT7, an antibody specific to human tau (Innogenetics (Cosmo Bio Co., Ltd), an antibody specific to mouse tau (1:1,000, produced in the Inventors' laboratory) and 12E8, an antibody against pS262 (1:1,000, produced in the Inventors' laboratory) were also used.

Figure 2:
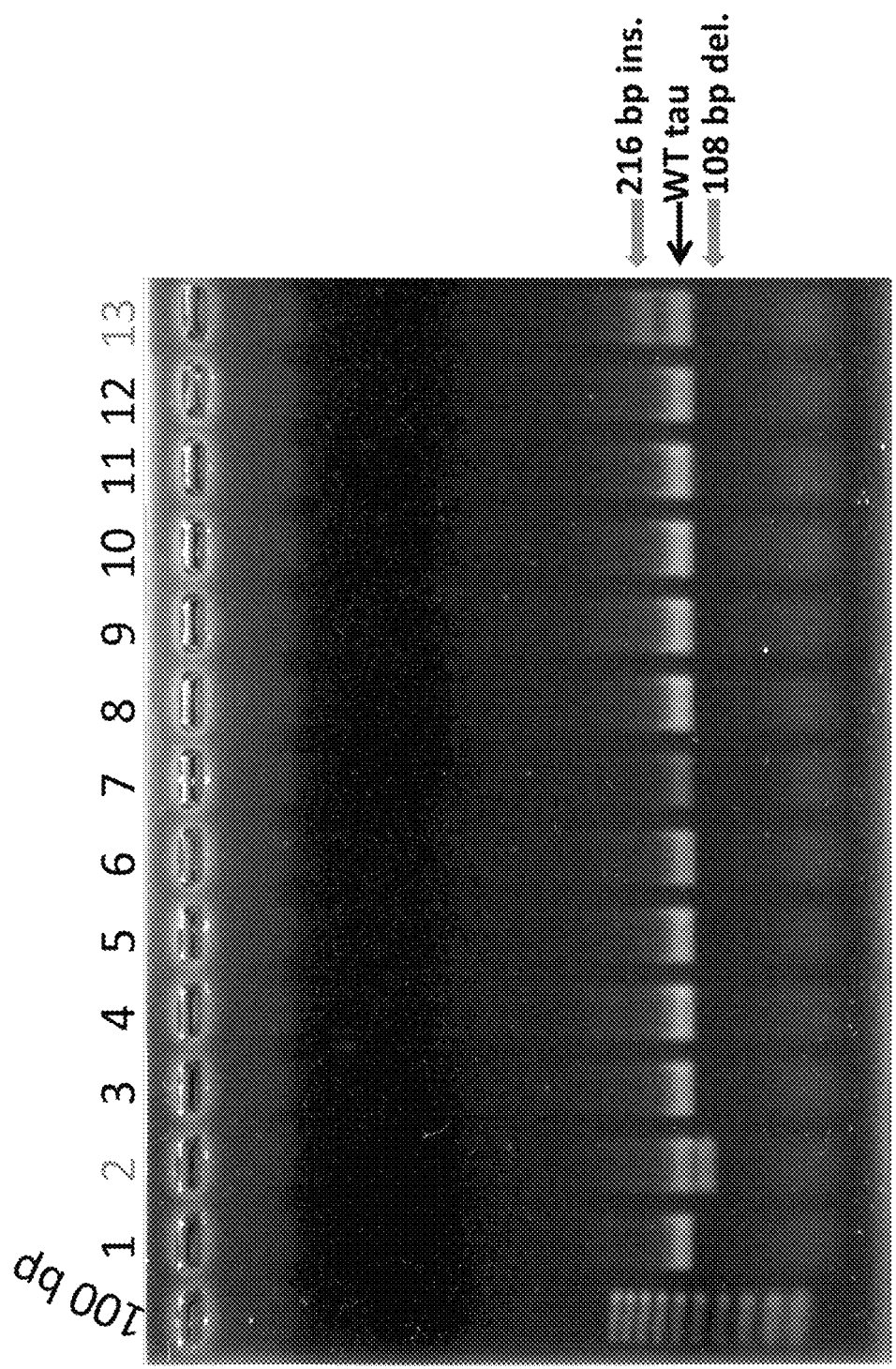
FIG. 2 is an electrophoretogram of PCR products obtained by amplifying genomic DNAs, as templates, of mouse pups obtained by injecting sgRNA-6 and Cas 9 mRNAs into fertilized mouse eggs at the pronuclear stage and by transferring the eggs into pseudopregnant mouse uterus to develop to term.

(1.2) Results (1.2.1) Production of Tau 3R/4R Mutant Mice 26 newborn mouse pups were born following microinjection of tau sgRNA and Cas 9 mRNA. PCR was conducted for the genotyping and PCR products were examined by electrophoresis. A part of the results was shown in FIG. 2. FIG. 2 is an electrophoretogram of PCR products obtained by amplifying genomic DNAs of pups #1 to #13 of the 26 pups, as template using a pair of primes with nucleotide sequences recited in SEQ ID Nos: 3 and 4 in each lane with 100 bp DNA size markers run on the left side lane. #2 and "13, which were readily recognized to have mutations by PCR, were selected and their offsprings were bred for further analysis.

By DNA sequencing, it was found that #2 mutant strain carries a 107 bp deletion and #13 mutant strain carries a 211 bp insertion and a four bp deletion between 3' terminal side of the tenth exon and the tenth intron of tau gene. Neither #2 nor #13 was detected to contain DNA derived from the plasmid in which donor DNA of SEQ ID NO: 11 was inserted into pBluescript II SK (+) vector. Accordingly, it was considered that the mutation in the mouse tau gene found in #2 and #13 were induced solely by CRISPR-Cas 9 system. FIG. 3 is a sequence alignment, prepared by Clustal X, of chromosomal DNA in the region from the tenth exon to the tenth intron of tau gene comparing Tau 3R/4R #2 and #13 with wild-type C57BL/6J strain. In both #2 and #13, 5' splicing donor site was destroyed due to genome editing in the region between the tenth exon and the tenth intron. #13 also has a stop codon in the middle of the tenth exon. It was predicted, accordingly, that the tenth exon was not functioning in both mutant strains.

(1.2.2) Analysis of Tau Isoforms Expressed in the Tau 3R/4R Mutant Mice

Figure 4:
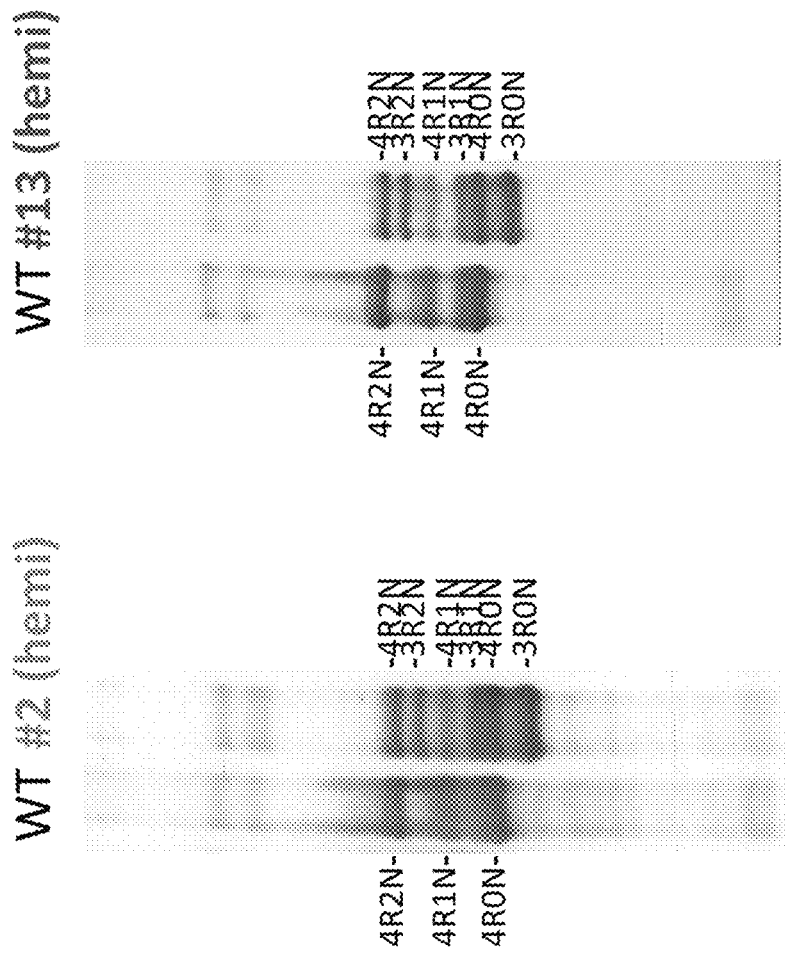
FIG. 4 is an immunoblot result obtained by extracting protein samples from adult brains of hemizygotes of #2 (#2 hemi) and #13 (#13 hemi) mutant mice and a wild type mouse (WT); dephosphorylating the protein samples with alkaline phosphorylase; separating the protein samples by electrophoresis; transferring the separated samples to a membrane; and staining the membrane with T46, an antibody against total tau.

FIG. 4 is an immunoblot result obtained by extracting protein samples from adult brains of hemizygotes of #2 strain (#2 hemi) and #13 strain (#13 hemi) mice and a wild type mouse (VVT); dephosphorylating the protein samples with alkaline phosphorylase; separating the protein samples by electrophoresis; transferring the separated samples to a membrane; and staining the membrane with T46, an antibody against total tau. As shown in FIG. 4, only three isoforms of 4R type tau were detected in the brain of the wild-type mice. In addition to the three isoforms of 4R type tau, three isoforms of 3R type tau were also detected in the brains of hemizygotes of #2 strain (#2 hemi) and #13 strain (#13 hemi) mice. In other words, the hemizygotes of #2 and #13 expressed six isoforms of 3R and 4R type tau in their brains just as in the human brain.

Figure 5:
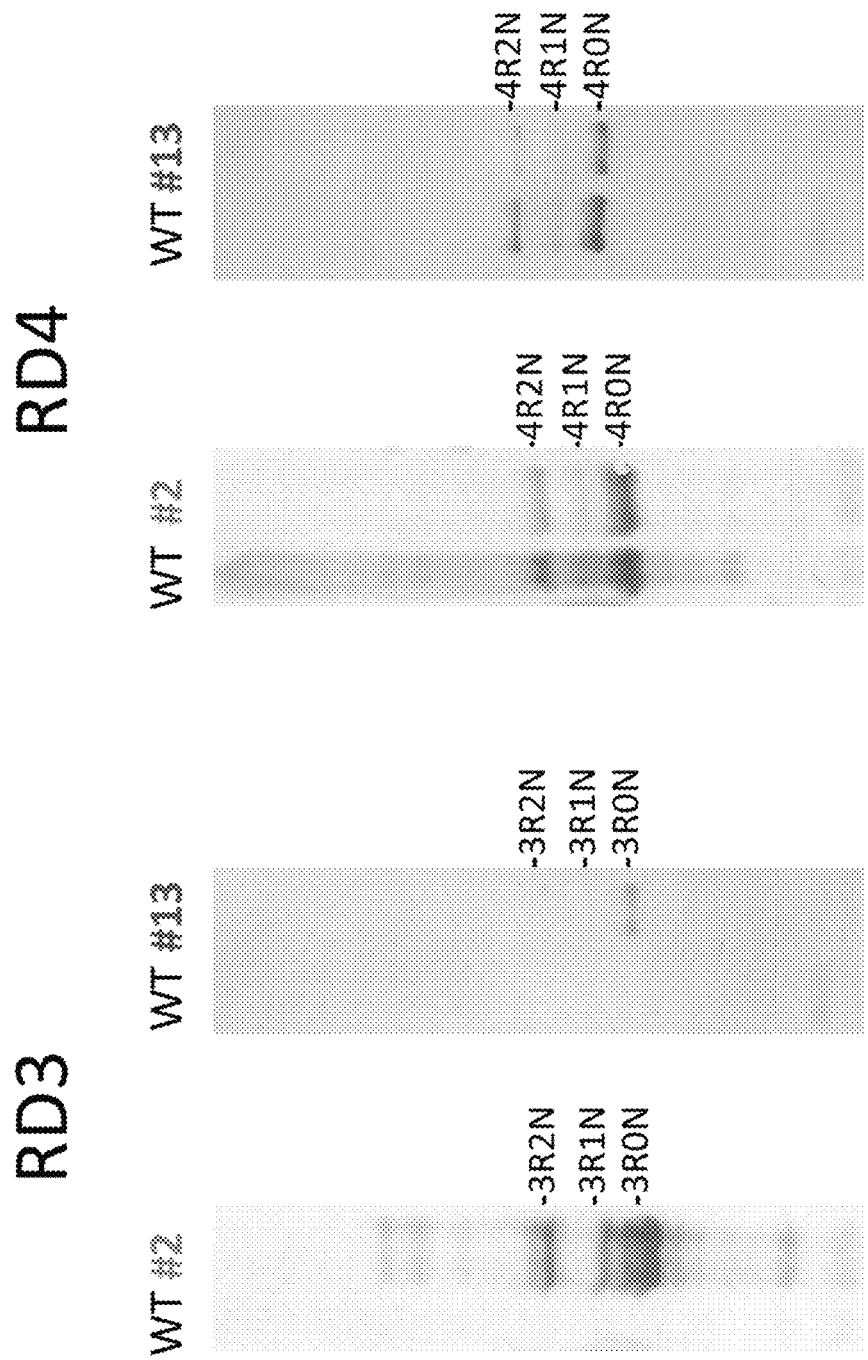
FIG. 5 is an immunoblot result with the same protein samples as FIG. 4, except that an antibodies specific to 3R type tau (RD3) and 4R type tau (RD4) were used.

FIG. 5 is an immunoblot result with the same protein samples as FIG. 4, except that an antibodies specific to 3R type tau (RD3) and 4R type tau (RD4) were used. As shown in FIG. 5, 4R type tau, but not 3R type tau, was detected in the adult brain of the wild-type mouse, while both 3R and 4R type tau were detected in the adult brain of the hemizygotes of both #2 and #13.

Figure 6:
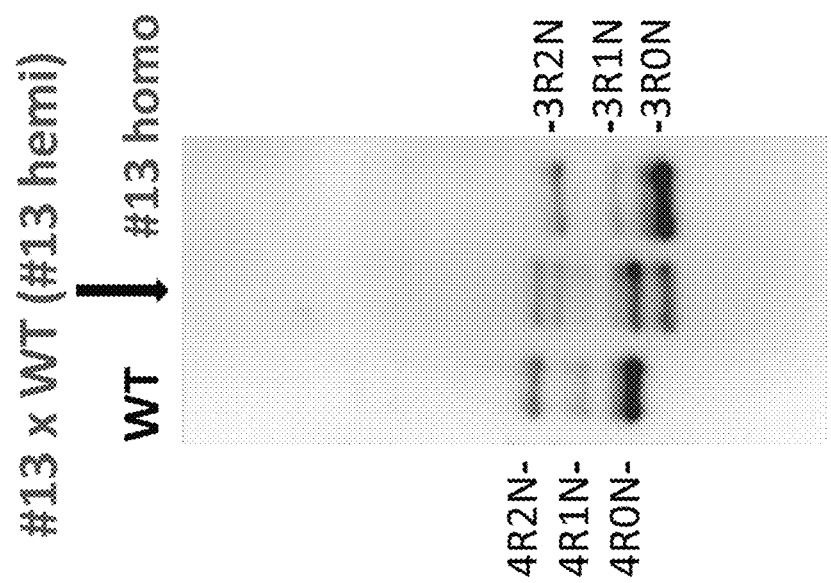
FIG. 6 is an immunoblot result obtained by extracting protein samples from adult brains of a hemizygote mouse of #13 (#13 hemi) and a homozygote mouse of #13 (#13 homo) and wild type mouse (WT); dephosphorylating the protein samples with alkaline phosphorylase; separating the protein samples by electrophoresis; transferring the separated protein samples to a membrane; and staining the membrane with T46, an antibody against total tau.

FIG. 6 is an immunoblot result obtained by extracting protein samples from adult brains of a hemizygote mouse of #13 (#13 hemi) and a homozygote mouse of #13 (#13 homo) and wild type mouse (VVT); dephosphorylating the protein samples with alkaline phosphorylase; separating the protein samples by electrophoresis; transferring the separated samples to a membrane; and staining the membrane with T46, an antibody against total tau. All three isoforms of 3R type tau, but no isoform of 4R type tau, were detected in the adult brain of a homozygote of disrupted tenth exon produced by breeding the hemizygote mice with the disrupted tenth exon. These results successfully confirmed that #2 and

13 strains are Tau 3R/4R mutant mice which reproduce the expression pattern of tau protein isoform types of adult human brain, that is, approximately equal amounts of 3R type tau and 4R type tau are expressed in the adult brain. #2 and #13 strains of Tau 3R/4R mutant mice were deposited with the Patent Microorganisms Depositary of National Institute of Technology and Evaluation (NPMD) on Feb. 27, 2019, and accession numbers NITE AP-02897 and NITE AP-02898 for the national deposits were assigned for Tau 3R/4R #2 and #13, respectively. Further, the national deposits were converted to international deposits made under the Budapest Treaty on Feb. 26, 2020, with international accession numbers NITE BP-02897 and NITE BP-02898, respectively.

Figure 7:
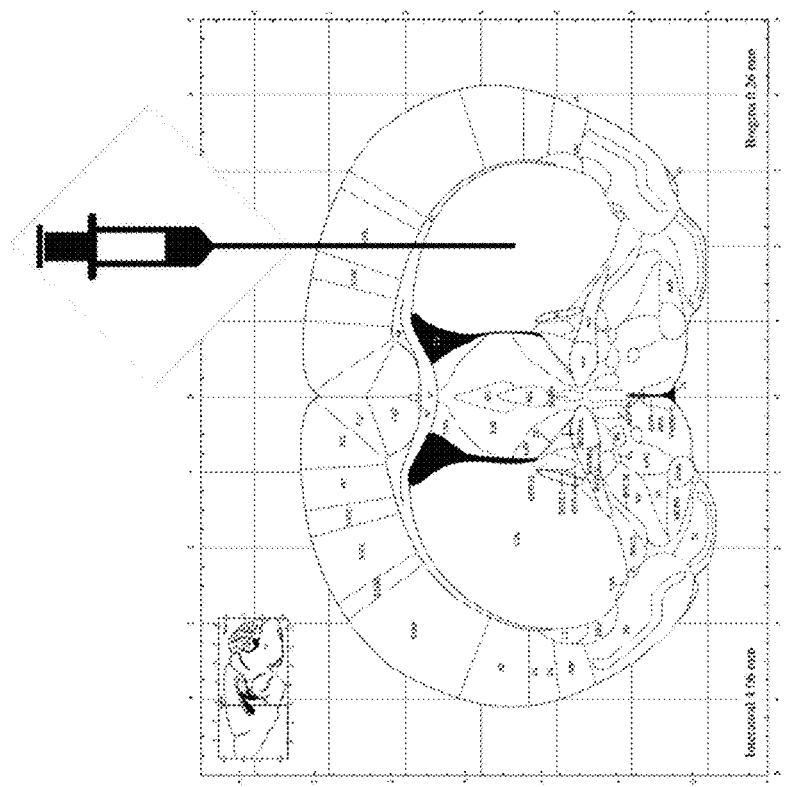
FIG. 7 is a schematic illustration of injecting tau seeds with a Hamilton syringe into the right striatum of an adult mouse brain as shown in a coronal sectional view.

Example 2 Injection of Tau Seeds Derived from Brain of Human Patient with Tauopathy Using Tau 3R/4R Mutant Mice (2.1) Injection of Tau Seeds Derived from Brain of Human AD Patient to the Tau 3R/4R Mice FIG. 7 is a schematic illustration of injecting a tau seed with a Hamilton syringe into the right striatum of an adult mouse brain as shown in a coronal sectional view. In the following examples, hemizygotes of #13 strain was used as the Tau 3R/4R mutant mice. Sarkosyl insoluble fractions (5 microliter) of brain of AD patient as tau seeds were injected into right striatum of hemizygotes of Tau 3R/4R #13 strain. The mice were anesthetized by inhaling isoflurane. Anesthesia was performed with induction anesthesia: 4 vol. %, 0.4 L/min., and maintenance anesthesia: 2 vol. %, 0.2 L/min. Animals were held to a brain stereotaxis apparatus (stoelting, 51600/51615). Injection site was determined based on Franklin, K. B. J. and Paxinos, G. (The Mouse Brain in Stereotaxic Coordinates, 4th ed., 2012, Academic Press). To inject into right striatum of a mouse, the condition was set to: A-P: +0.2 mm, M-L: +2.0 mm, D-V: −2.6 mm. 5 microliter of the tau seeds suspension was injected using a 10 microliter Hamilton syringe (HAMILTON, #80330). The brain was dissected eight months after injection, fixed in 4% paraformaldehyde, thin sliced and subjected to immunohistochemical staining with an antibody against phosphorylated tau (AT8).

Figure 8:
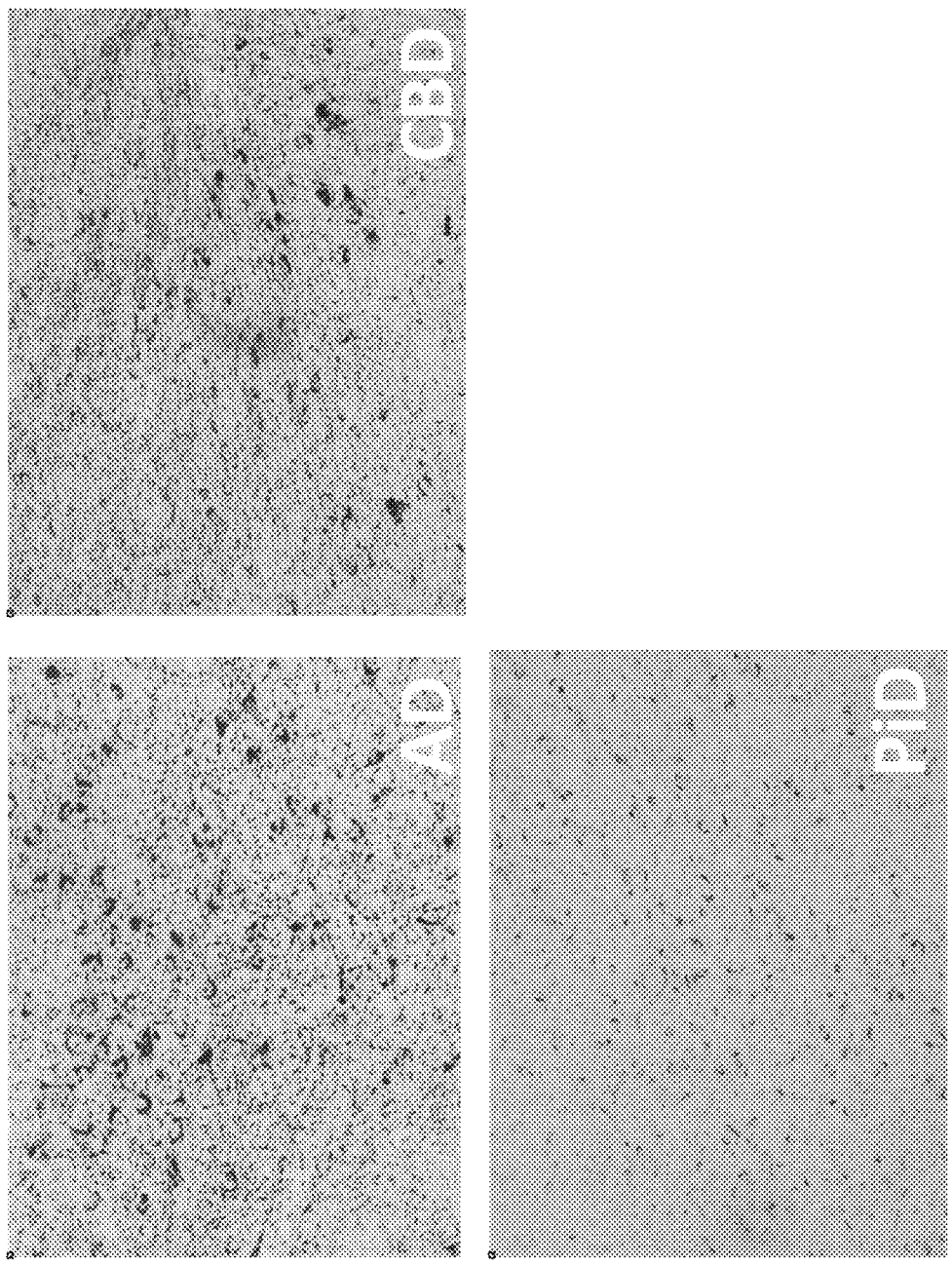
FIG. 8 is a combination of microscopic photographs of tissue specimens of right striatum of the Tau 3R/4R mutant mouse brains prepared by injecting tau seeds derived from human brains of patients with Alzheimer's Disease (AD), corticobasal degeneration (CBD) and Pick's disease (PiD) into the right striatum of the mutant mouse brains; dissecting the mutant mouse brains eight months after injection; fixing the mutant mouse brains in 4% paraformaldehyde; sectioning; and staining the tissue specimens immunohistochemically with an antibody against phosphorylated tau (AT8).

FIG. 8 is a combination of microscopic photographs of tissue specimens of right striatum of the Tau 3R/4R mutant mouse brains prepared by injecting tau seeds derived from human brains of patients with Alzheimer's Disease (AD), corticobasal degeneration (CBD) and Pick's disease (PiD) into the right striatum of the mutant mouse brains; dissecting the mutant mouse brains eight months after injection; fixing in 4% paraformaldehyde; sectioning; and staining the tissue specimens immunohistochemically with an antibody against phosphorylated tau (AT8). As shown in FIG. 8, the pathological tau fibrils were deposited in the injection site of right striatum, when any of the tau seeds derived from brains of patients with tauopathies was injected.

Figure 9:
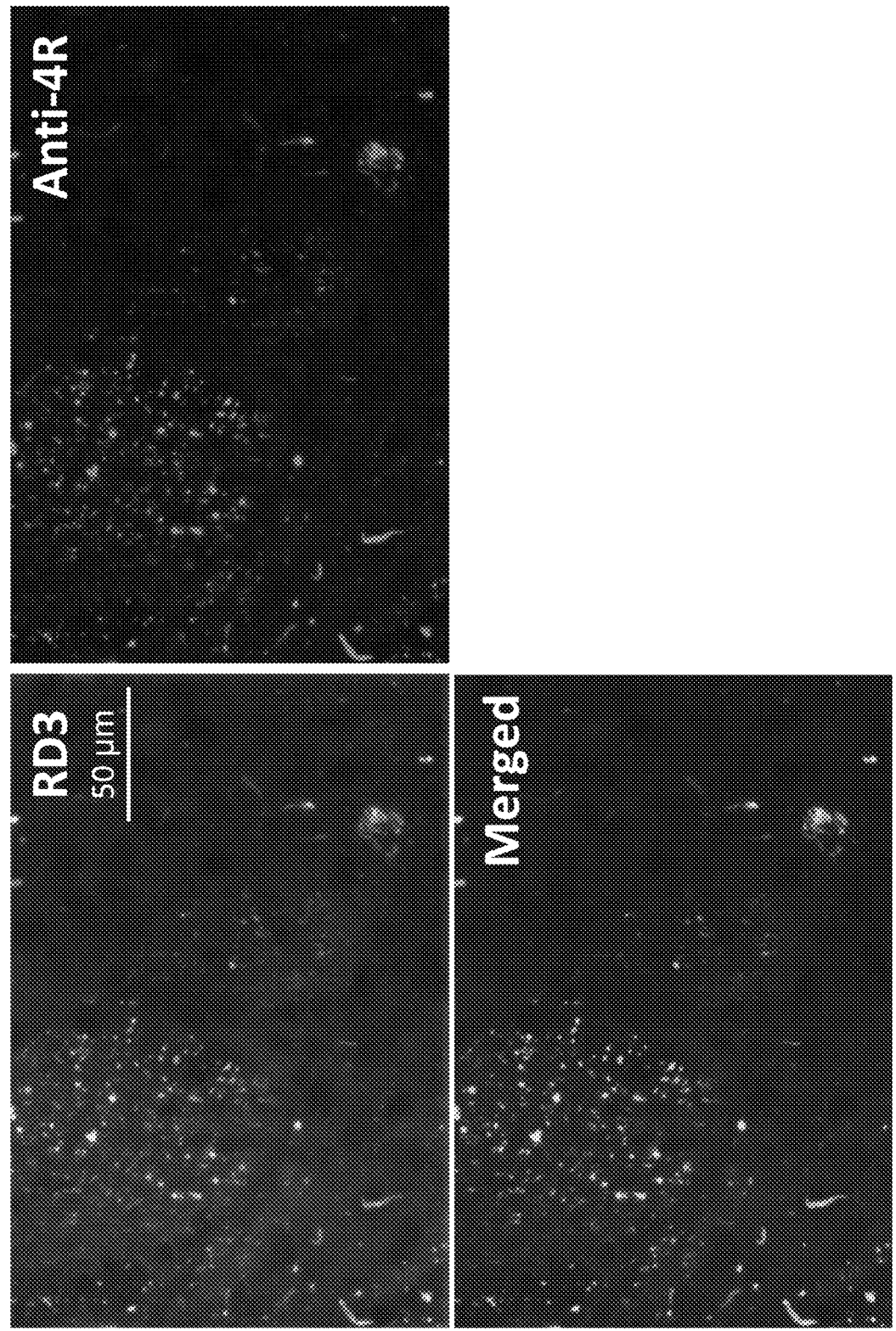
FIG. 9 is a combination of microscopic photographs of the identical field of view for a tissue specimen of right striatum of the Tau 3R/4R mutant mouse brains prepared by injecting tau seeds derived from a human brain of a patient with Alzheimer's Disease (AD) into the right striatum of the mouse brains; dissecting the mouse brains six months after injection; fixing the mouse brains in 4% paraformaldehyde; sectioning; and staining the tissue specimens immunohistochemically with antibodies specific for 3R tau and 4R type tau (RD3 and anti-4R, respectively) which are labeled with distinct fluorescent dyes respectively.

FIG. 9 is a combination of microscopic photographs of the identical field of view for a tissue specimen of right striatum of the Tau 3R/4R mutant mouse brains prepared by injecting tau seeds derived from a human brain of a patient with Alzheimer's Disease (AD) into the right striatum of the mouse brains; dissecting the mouse brains six months after injection; fixing the mouse brains in 4% paraformaldehyde; sectioning; and staining the tissue specimens immunohistochemically with antibodies specific for 3R tau and 4R type tau (RD3 and anti-4R, respectively) which are labeled with distinct fluorescent dyes respectively. In FIG. 9, the upper left panel shows a fluorescent microscopic photograph observed under the condition which only detects the fluorescent dye labeled for the antibody specific for the 3R type tau (RD3); the upper right panel shows a fluorescent microscopic photograph observed under the condition which only detects the fluorescent dye labeled for the antibody specific for the 4R type tau (anti-4R); the lower left panel shows an image prepared by merging the upper left and upper right panels (merged). As shown in FIG. 9, when the tau seeds derived from human brain of an AD patient was injected to the Tau 3R/4R mutant mice, the pathological tau fibrils were formed which comprise 3R type tau and 4R type tau, which were observed to be co-localized.

Figure 10:
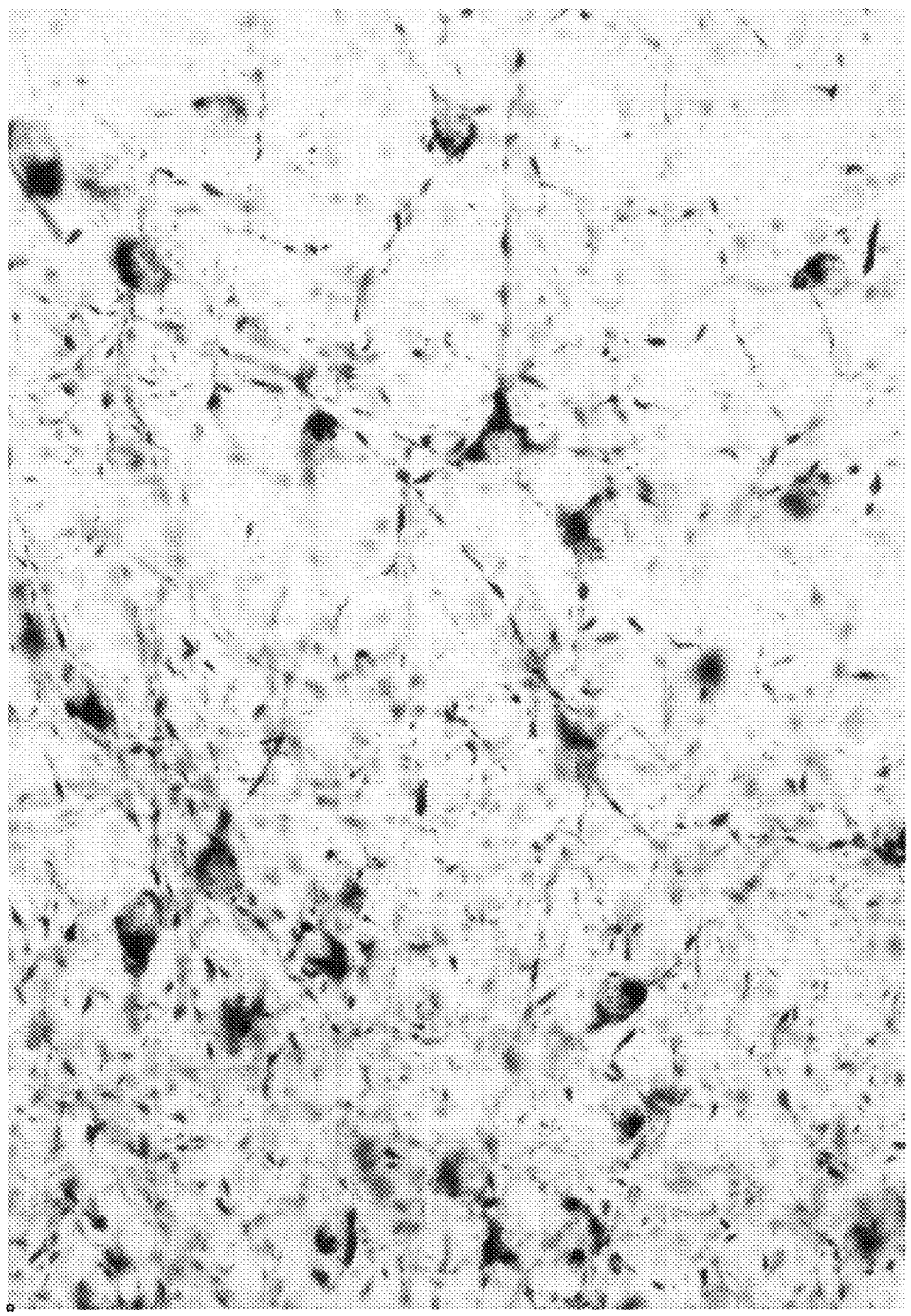
FIG. 10 is a microscopic photograph of a tissue specimen of right striatum of the Tau 3R/4R mutant mouse brains prepared by injecting tau seeds derived from a human brain of a patient with Alzheimer's Disease (AD) comprising equal amounts of 3R type tau and 4R type tau into the right striatum of the mutant mouse brains; dissecting the mutant mouse brains eight months after injection; fixing the mouse brains in 4% paraformaldehyde; sectioning; and staining the tissue specimens immunohistochemically with an antibody against phosphorylated tau (AT8).

FIG. 10 is a microscopic photograph of a tissue specimen of right striatum of the Tau 3R/4R mutant mouse brains prepared by injecting tau seeds derived from a human brain of a patient with Alzheimer's disease (AD) comprising equal amounts of 3R type tau and 4R type tau into the right striatum of the mutant mouse brains; dissecting the mutant mouse brains eight months after injection; fixing the mouse brains in 4% paraformaldehyde; sectioning; and staining the tissue specimens immunohistochemically with an antibody against phosphorylated tau (AT8). As shown in FIG. 10, when the tau seeds derived from human brain of an AD patient was injected to the Tau 3R/4R mutant mice, neurofibrillary tangles, a pathohistological manifestation characteristic of Alzheimer's Disease (AD), were observed in the mouse brain.

Figure 11:
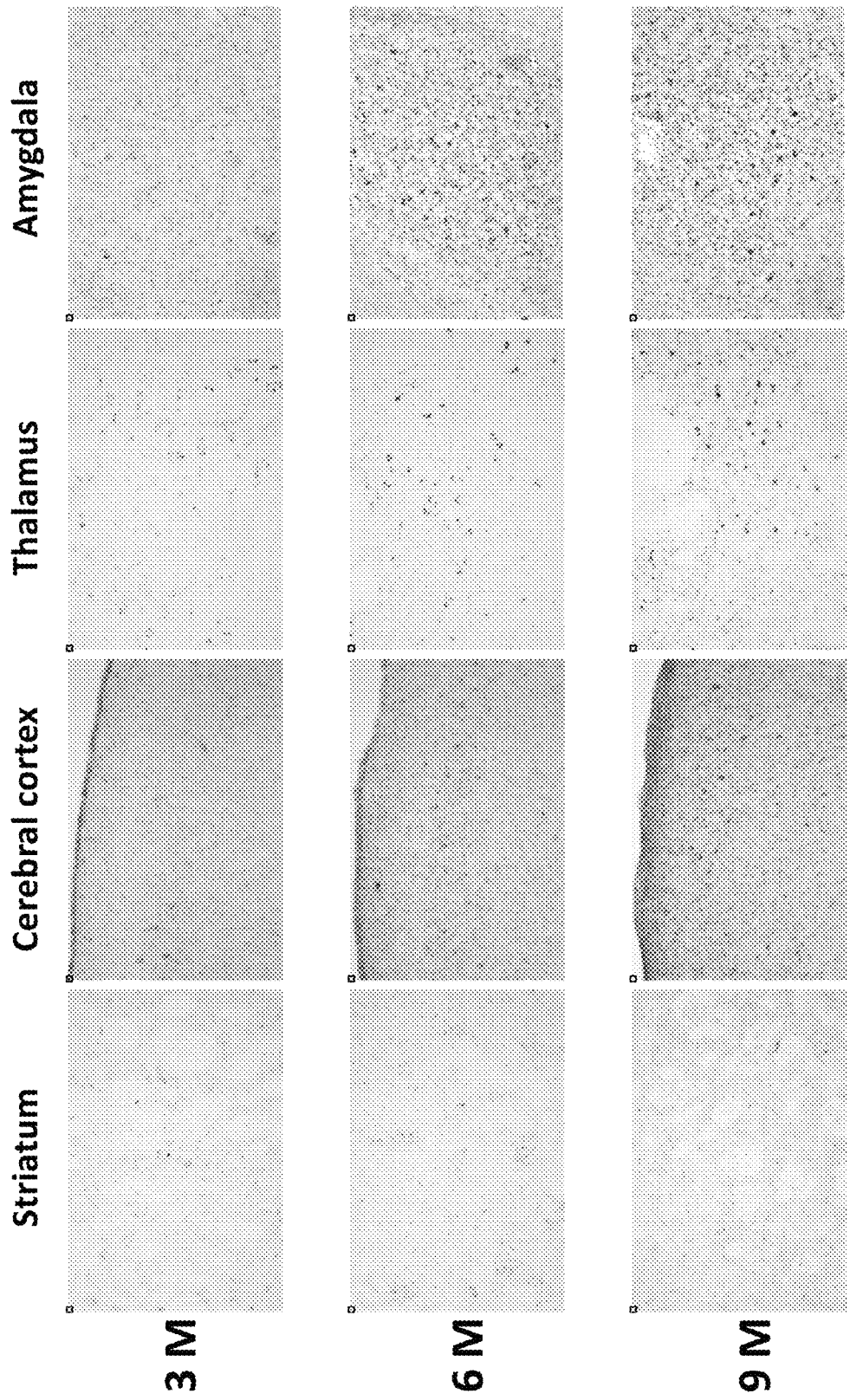
FIG. 11 is a combination of microscopic photographs of tissue specimens of right striatum (Striatum), cerebral cortex (Cerebral cortex), thalamus (Thalamus) and amygdala (Amygdala) of the Tau 3R/4R mutant mouse brains prepared by injecting tau seeds derived from a human brain of a patient with Alzheimer's Disease (AD) into the right striatum of the mutant mouse brains; dissecting the mutant mouse brains three, six and nine months (3M, 6M and 9M, respectively) after injection; fixing the mouse brains in 4% paraformaldehyde; sectioning; and staining the tissue specimens immunohistochemically with an antibody against phosphorylated tau (AT8).

(2.2) Propagation of the Deposition of the Pathological Tau Fibrils in the Brain Using the Tau 3R/4R Mutant Mouse FIG. 11 is a combination of microscopic photographs of tissue specimens of right striatum (Striatum), cerebral cortex (Cerebral cortex), thalamus (Thalamus) and amygdala (Amygdala) of the Tau 3R/4R mutant mouse brains prepared by injecting tau seeds derived from a human brain of a patient with Alzheimer's disease (AD) into the right striatum of the mutant mouse brains; dissecting the mutant mouse brains three, six and nine months (3M, 6M and 9M, respectively) after injection; fixing the mouse brains in 4% paraformaldehyde; sectioning; and staining the tissue specimens immunohistochemically with an antibody against phosphorylated tau (AT8). As shown in FIG. 11, it was observed that the pathological tau fibrils were formed in striatum, cerebral cortex and thalamus three months after injection, as well as amygdala six months after injection, and that the formation of the pathological tau fibrils was enhanced as the time passed by after injection.

(2.3) Seed Dependent Deposition of Pathological Tau Fibrils

Figure 12:
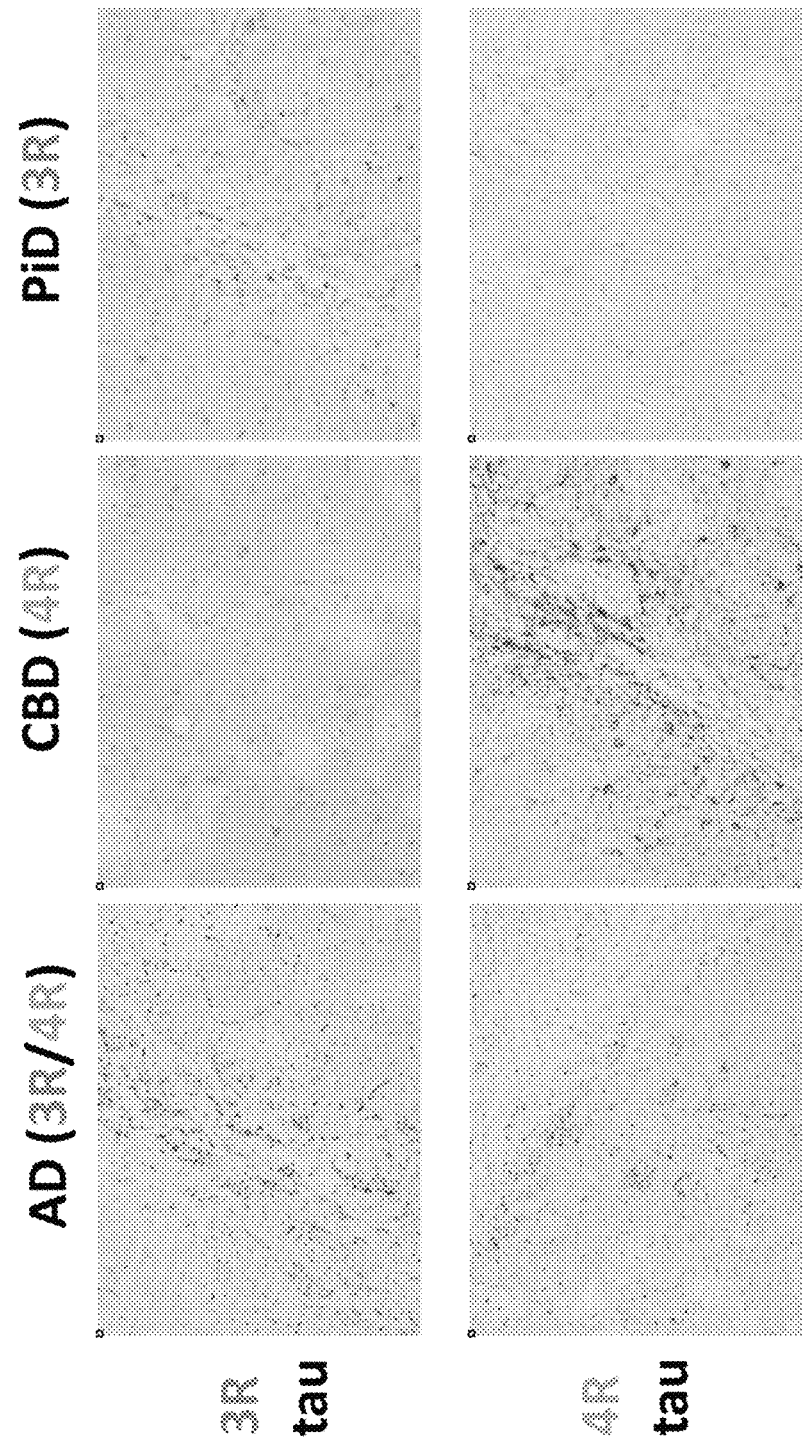
FIG. 12 is a combination of microscopic photographs of tissue specimens of right striatum of the Tau 3R/4R mutant mouse brains prepared by injecting tau seeds derived from human brains of patients with Alzheimer's Disease (AD), corticobasal degeneration (CBD) and Pick's disease (PiD) into the right striatum of the mutant mouse brains; dissecting the mutant mouse brains nine months after injection; fixing the mutant mouse brains in 4% paraformaldehyde; sectioning; and staining the tissue specimens immunohistochemically with an antibody specific for 3R type tau (3R tau) or 4R type tau (4R tau).

As described in the above, it has been known that different tauopathy disease has different isoform composition of the tau protein in the pathological tau fibrils deposited in the human brain of patients with tauopathies. Namely, equal amounts of 3R type and 4R type are deposited in the brain of AD, only 3R type is deposited in the brain of PiD, and only 4R type is deposited in the brain of CBD and PSP. FIG. 12 is a combination of microscopic photographs of tissue specimens of right striatum of the Tau 3R/4R mutant mouse brains prepared by injecting tau seeds derived from human brains of patients with Alzheimer's disease (AD), corticobasal degeneration (CBD) and Pick's disease (PiD) into the right striatum of the mutant mouse brains; dissecting the mutant mouse brains nine months after injection; fixing the mutant mouse brains in 4% paraformaldehyde; sectioning; and staining the tissue specimens immunohistochemically with an antibody specific for 3R type tau (3R tau) or 4R type tau (4R tau). As shown in FIG. 12, 3R type and 4R type tau were comprised in the pathological tau fibrils formed by the injection to the Tau 3R/4R mutant mice of the tau seeds derived from a human brain of a AD patient, in whose brain equal amounts of 3R type and 4R type were deposited. Only 4R type tau was comprised in the pathological tau fibrils formed by the injection to the Tau 3R/4R mutant mice of the tau seeds derived from a human brain of a CBD patient, in whose brain only 4R type was deposited. Only 3R type tau was comprised in the pathological tau fibrils formed by the injection to the Tau 3R/4R mutant mice of the tau seeds derived from a human brain of a PiD patient, in whose brain only 3R type was deposited. By using the Tau 3R/4R mutant mice, therefore, it was demonstrated in vivo that, depending on the tau seeds with 3R type, 4R type or both 3R type and 4R type, the resulting pathological tau fibrils comprise 3R type tau alone or 4R type tau alone, or both 3R type and 4R type tau.

(2.4) Induction of the Pathological Tau Fibrils by Injecting Human Tau Seed

Figure 13:
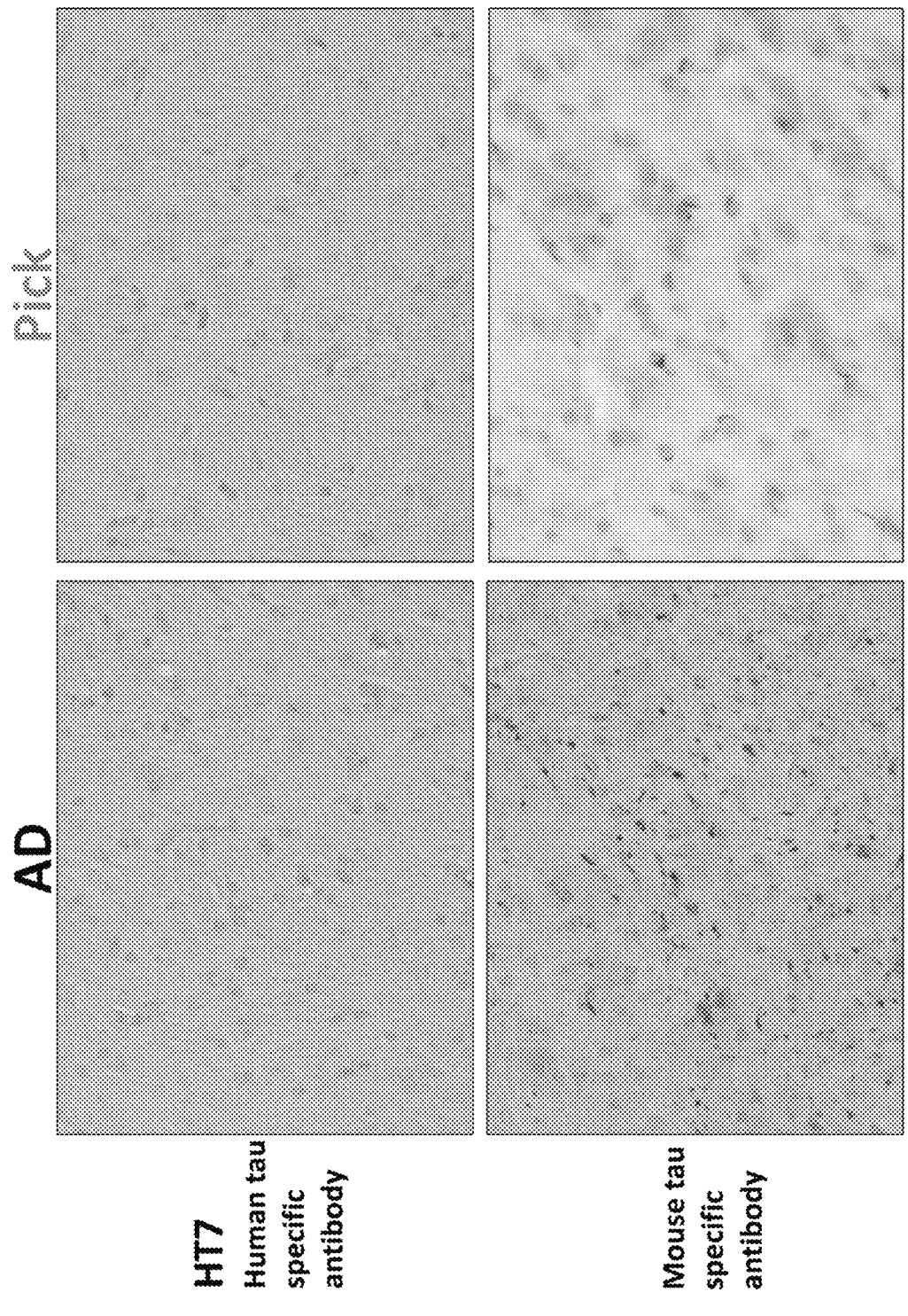
FIG. 13 is a combination of microscopic photographs of tissue specimens of right striatum of the Tau 3R/4R mutant mouse brains prepared by injecting tau seeds derived from human brains of patients with Alzheimer's Disease (AD) and Pick's disease (Pick) into the right striatum of the Tau 3R/4R mutant mouse brains; dissecting the mutant mouse brains eight months after injection; fixing the mutant mouse brains in 4% paraformaldehyde; sectioning; and staining the tissue specimens immunohistochemically with an antibody specific for human tau (HT7) or mouse tau (prepared in the Inventors' laboratory).

FIG. 13 is a combination of microscopic photographs of tissue specimens of right striatum of the Tau 3R/4R mutant mouse brains prepared by injecting tau seeds derived from human brains of patients with Alzheimer's disease (AD) and Pick's disease (Pick) into the right striatum of the Tau 3R/4R mutant mouse brains; dissecting the mutant mouse brains eight months after injection; fixing the mutant mouse brains in 4% paraformaldehyde; sectioning; and staining the tissue specimens immunohistochemically with an antibody specific for human tau (HT7) or mouse tau (prepared in the Inventors' laboratory). As shown in FIG. 13, regardless of injecting the tau seeds derived from a human brain of a AD patient, in whose brain equal amounts of 3R type and 4R type were deposited, or the tau seeds derived from a human brain of a PiD patient, in whose brain only 3R type was deposited, only mouse tau was detected in the resulting pathological tau fibrils, and not human tau. Therefore, it is considered that the human tau comprised in the injected tau seeds were degraded and that mouse tau produced in the Tau 3R/4R mutant mice is aggregated to form the pathological tau fibrils.

(2.5) Reproduction of Human Pathogenesis

Figure 14:
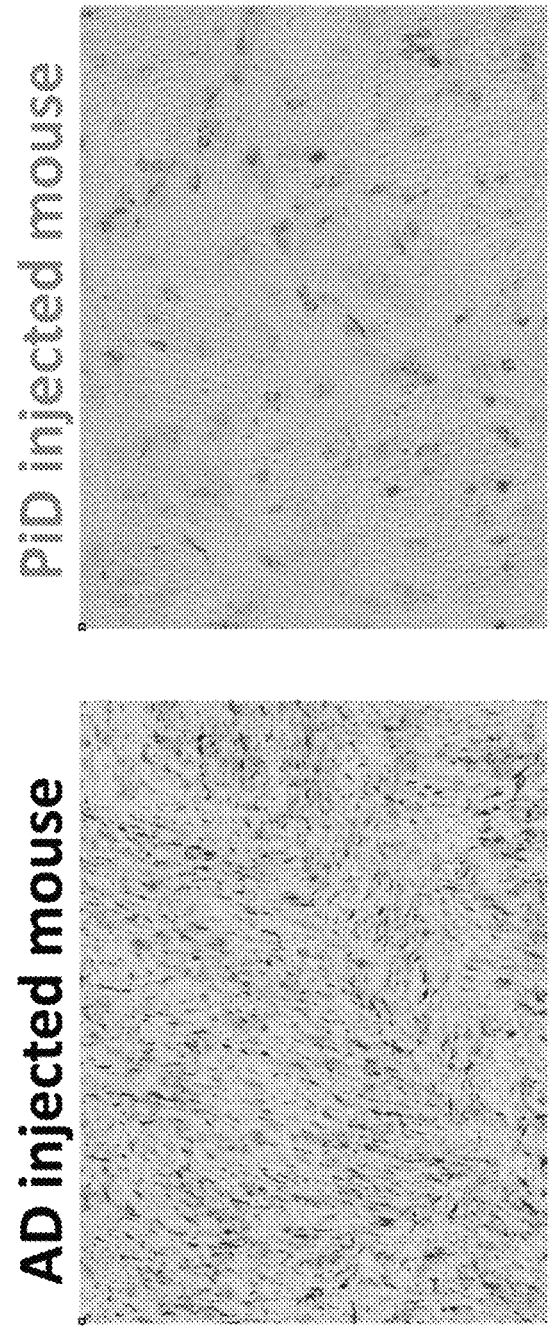
FIG. 14 is a combination of microscopic photographs of tissue specimens of right striatum of the Tau 3R/4R mutant mouse brains prepared by injecting tau seeds derived from human brains of patients with Alzheimer's Disease (AD) and Pick's disease (Pick) into the right striatum of the Tau 3R/4R mutant mouse brains; dissecting the mutant mouse brains eight months after injection; fixing the mutant mouse brains in 4% paraformaldehyde; sectioning; and staining the tissue specimens by Gallyas-Braak silver staining method.

We examined whether the disease model animal of the present invention of tauopathies may mimic the negative Gallyas-Braak silver staining in the brain of patients with Pick's disease, as reported previously. FIG. 14 is a combination of microscopic photographs of tissue specimens of right striatum of the Tau 3R/4R mutant mouse brains prepared by injecting tau seeds derived from human brains of patients with Alzheimer's disease (AD) and Pick's disease (Pick) into the right striatum of the Tau 3R/4R mutant mouse brains; dissecting the mutant mouse brains eight months after injection; fixing the mutant mouse brains in 4% paraformaldehyde; sectioning; and staining the tissue specimens by Gallyas-Braak silver staining method. As shown in FIG. 14, Gallyas-Braak silver staining was positive regarding the mouse brain injected with human AD tau, but the same staining was negative regarding the mouse brain injected with tau seeds of human Pick's disease.

Figure 15:
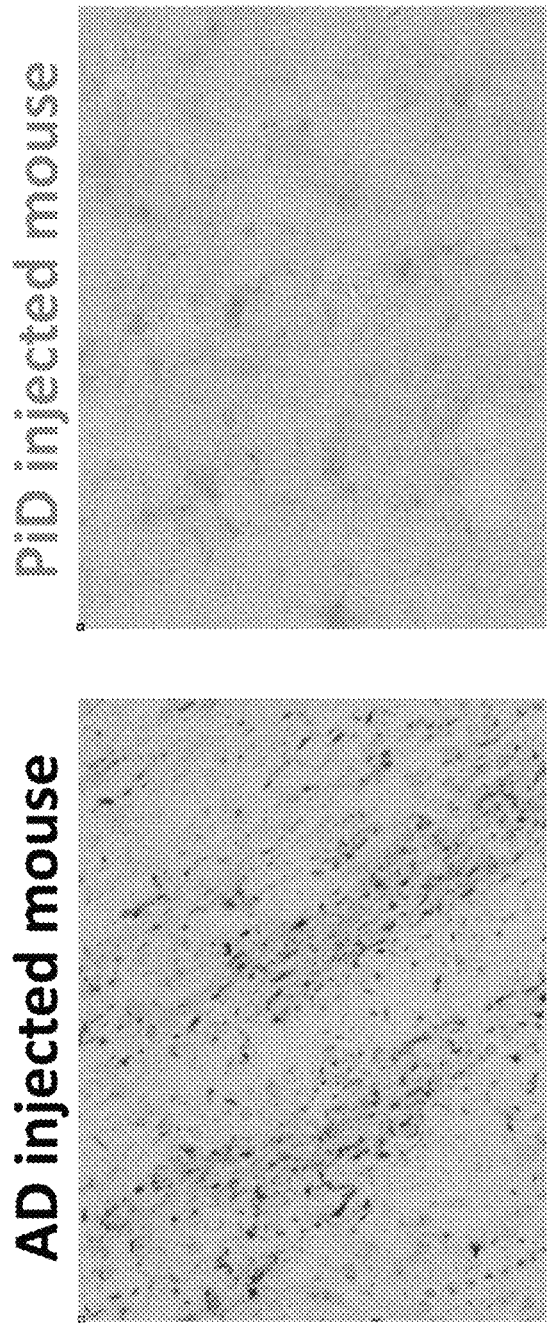
FIG. 15 is a combination of microscopic photographs of tissue specimens of right striatum of the Tau 3R/4R mutant mouse brains prepared by injecting tau seeds derived from human brains of patients with Alzheimer's Disease (AD) and Pick's disease (Pick) into the right striatum of the Tau 3R/4R mutant mouse brains; dissecting the mutant mouse brains eight months after injection; fixing the mutant mouse brains in 4% paraformaldehyde; sectioning; and staining the tissue specimens immunohistochemically with the 12E8 (pS262) antibody.

We also examined whether the disease model animal of tauopathies of the present invention may mimic the lack of phosphorylation at tau S262 in the brain of patients with Pick's disease, as reported. FIG. 15 is a combination of microscopic photographs of tissue specimens of right striatum of the Tau 3R/4R mutant mouse brains prepared by injecting tau seeds derived from human brains of patients with Alzheimer's Disease (AD) and Pick's disease (Pick) into the right striatum of the Tau 3R/4R mutant mouse brains; dissecting the mutant mouse brains eight months after injection; fixing the mutant mouse brains in 4% paraformaldehyde; sectioning the tissue of the ipsilateral striatum; and staining the tissue specimens immunohistochemically with the 12E8 (pS262) antibody. As shown in FIG. 15, an image was confirmed to show that S262 was phosphorylated in the pathological tau fibrils of the mouse brain injected with the tau seeds derived from human brain of an AD patient. No image, however, was observed to show that the antibody against phosphorylated S262 positively stained the pathological tau fibrils of the mouse brain injected with the tau seeds derived from human brain of a patient with Pick's disease. It was therefore considered that the disease model animal of the present invention of sporadic tauopathies successfully mimicked the properties of tau of Pick's disease, with regard to Gallyas-Braak silver staining and phosphorylation at tau S262.

FIG. 16 (left) is microscopic photographs of tissue specimens of right cerebral cortex of the Tau 3R/4R mutant mouse brains prepared by injecting tau seeds derived from human brains of patients with CBD, in which 4R type tau is deposited, into the Tau 3R/4R mutant mouse brains; dissecting the mutant mouse brains eight months after injection; fixing the mutant mouse brains in 4% paraformaldehyde; sectioning; and staining the tissue specimens immunohistochemically with an antibody against phosphorylated tau (AT8). FIG. 16 (right) is a microscopic photograph of typical astrocytic plaques observed in the brain of human patient with CBD. As the astrocytic plaques were formed in the mouse brain injected with the tau seeds derived from human brain of a patient with CBD as shown in FIG. 16 (left), similarly to the human brains of patients with CBD as shown in FIG. 16 (left), it was considered that the disease model animal of the present invention of sporadic tauopathies obtained by injecting the tau seed derived from human brain of a patient with CBD successfully mimicked the properties of the CBD tau, with regard to the astrocytic plaque formation.

Figure 17:
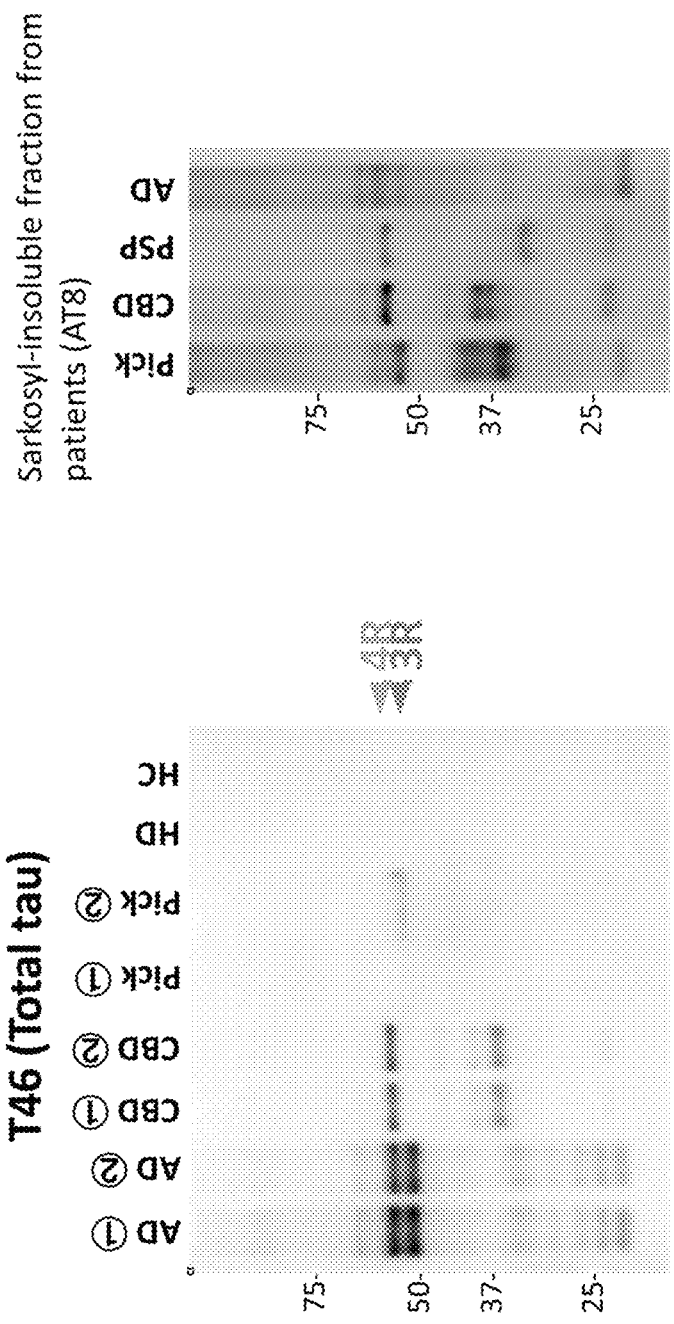
FIG. 17 (left) is an immunoblot result obtained by injecting tau seeds derived from patients with Alzheimer's Disease (AD), corticobasal degeneration (CBD) and Pick's disease (Pick) or healthy control human brain (HC) into the right striatum of the mutant mouse brains; dissecting the mutant mouse brains nine months after injection; preparing sarcosyl insoluble fractions; separating proteins in the sarcosyl insoluble fractions by electrophoresis; transferring the separated proteins to a membrane; and staining the membrane with T46, an antibody against total tau.
Figure 18:
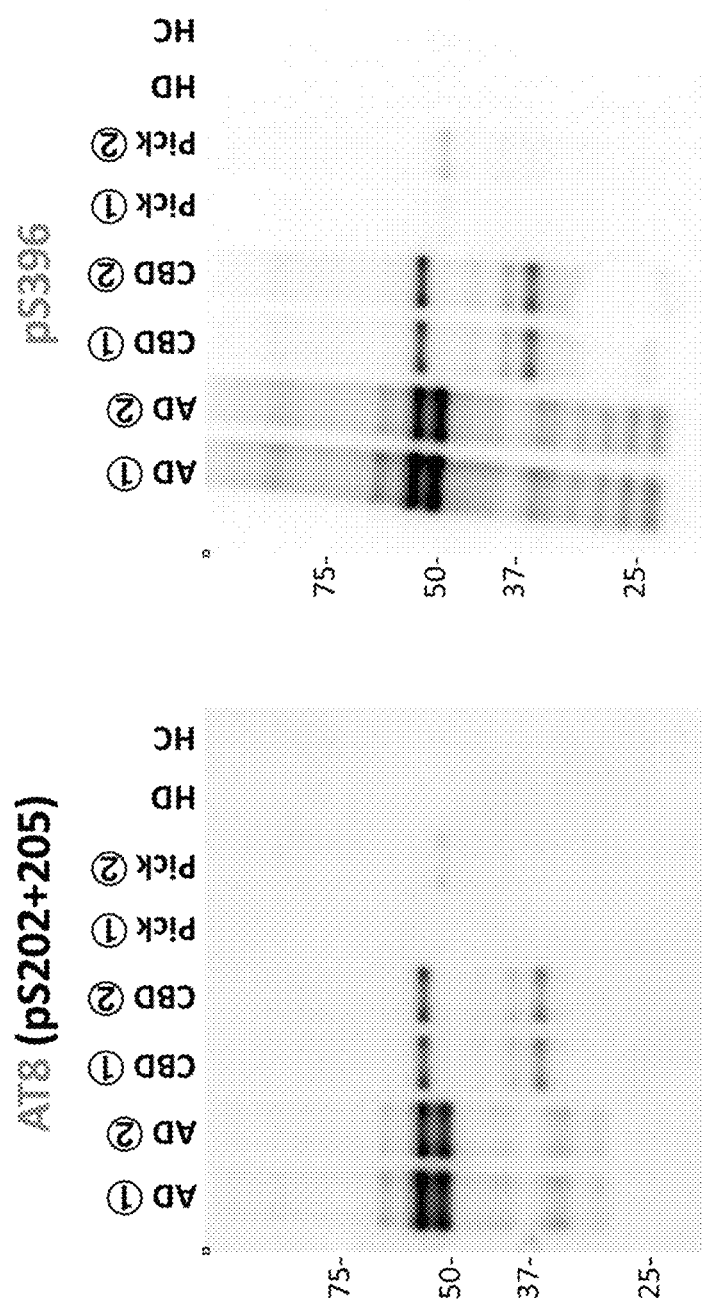
FIG. 18 is a pair of immunoblot results obtained by injecting tau seeds derived from patients with Alzheimer's Disease (AD), corticobasal degeneration (CBD), Pick's disease (Pick) and Huntington's disease (HD) or healthy control human brain (HC) into the right striatum of the mutant mouse brains; dissecting the mutant mouse brains nine months after injection; preparing sarcosyl insoluble fractions; separating proteins in the sarcosyl insoluble fractions by electrophoresis; transferring the separated proteins to a membrane; and staining the membrane with antibodies against phosphorylated tau (AT8 and pS396).
Figure 19:
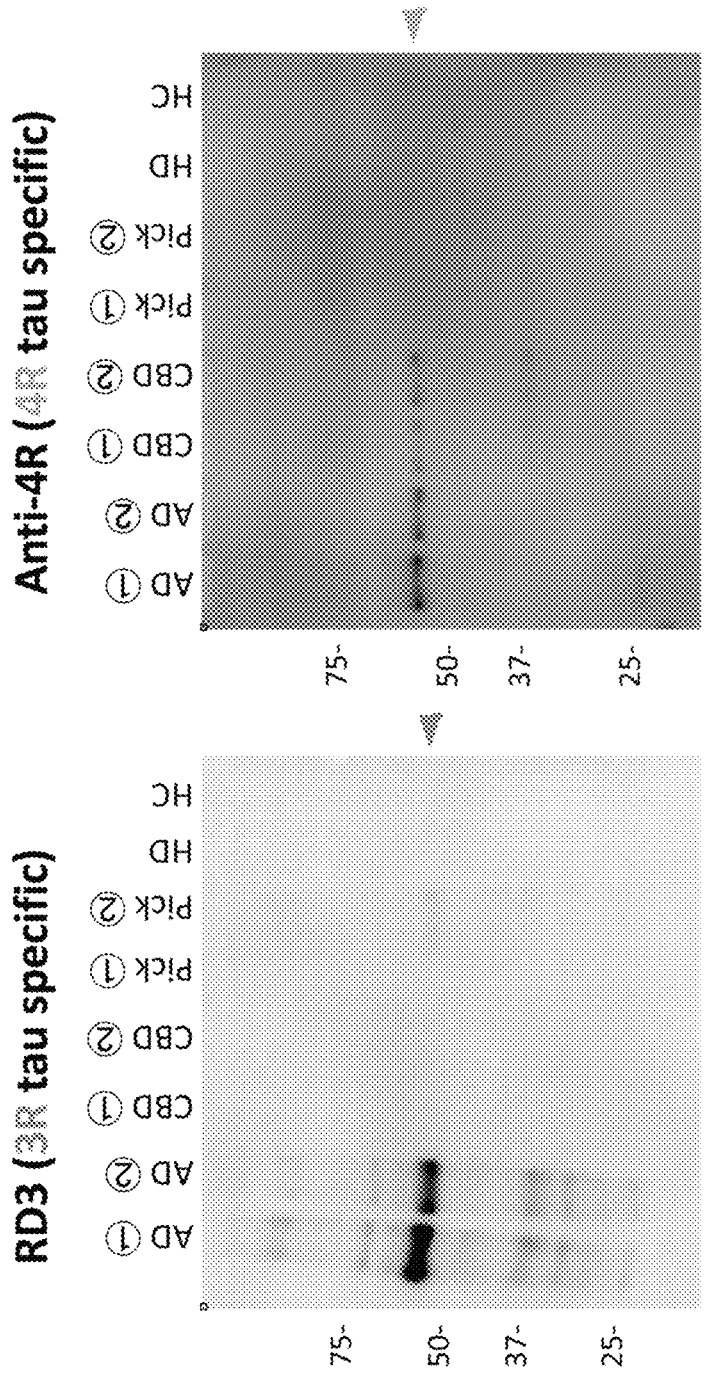
FIG. 19 is a pair of immunoblot results obtained by injecting tau seeds derived from patients with Alzheimer's Disease (AD), corticobasal degeneration (CBD), Pick's disease (Pick) and Huntington's disease (HD) or healthy control human brain (HC) into the right striatum of the mutant mouse brains; dissecting the mutant mouse brains nine months after injection; preparing sarcosyl insoluble fractions; separating proteins in the sarcosyl insoluble fractions by electrophoresis; transferring the separated proteins to a membrane; and staining the membrane with antibodies specific for 3R type tau (RD3) and 4R type tau (anti-4R).

Example 3 Biochemical Analysis (3.1) The Relationship of the Tau Isoform Type of the Injected Tau Seeds Derived from Patient Brain with the Tau Isoform Type of the Pathological Tau Fibrils Formed by the Tau Seeds Derived from the Patient Brain FIG. 17 (left), FIG. 18 and FIG. 19 are results obtained by injecting tau seeds derived from patients with Alzheimer's disease (AD), corticobasal degeneration (CBD), Pick's disease (Pick) and Huntington's disease (HD) or healthy control human brain (HC) into the right striatum of the Tau 3R/4R mutant mouse brains; dissecting the mutant mouse brains nine months after injection; preparing sarcosyl insoluble fractions; and immunoblotting with an antibody against total tau (T46), an antibody against phosphorylated tau (AT8 and pS396), an antibody specific to 3R type tau (RD3), and an antibody specific to 4R type tau (anti-4R). FIG. 17 (right) is an immunoblot result of sarcosyl insoluble fractions from human brain of the patients with Alzheimer's disease (AD), corticobasal degeneration (CBD) and Pick's disease (Pick) with an antibody against phosphorylated tau (AT8).

As shown in FIG. 17 (left), the antibody against total tau (T46) detected bands corresponding to the 3R type tau and 4R type tau in the sarcosyl insoluble fractions of the brain of a Tau 3R/4R mutant mouse injected with the tau seeds derived from the human brain of an AD patient, only a band corresponding to the 4R type tau in the sarcosyl insoluble fractions of the brain of a Tau 3R/4R mutant mouse injected with the tau seeds derived from the human brain of a CBD patient and only a band corresponding to the 3R type tau in the sarcosyl insoluble fractions of the brain of a Tau 3R/4R mutant mouse injected with the tau seeds derived from the human brain of a patient with Pick's disease.

As shown in FIG. 18, the antibodies against phosphorylated tau (AT8 and pS396) detected phosphorylated tau in the sarcosyl insoluble fractions of the brain of Tau 3R/4R mutant mice injected with the tau seeds derived from the human brain of patients with Alzheimer's Disease (AD), corticobasal degeneration (CBD) and Pick's disease (Pick).

As shown in FIG. 19 (left), the antibody specific to the 3R type tau (RD3) detected a band in the sarcosyl insoluble fractions of the brain of Tau 3R/4R mutant mice injected with the tau seeds derived from the human brain of a patient with Alzheimer's disease (AD) and Pick's disease (Pick). As shown in FIG. 19 (right), the antibody specific to the 4R type tau (anti-4R) detected a band in the sarcosyl insoluble fractions of the brain of Tau 3R/4R mutant mice injected with the tau seeds derived from the human brain of a patient with Alzheimer's disease (AD) and corticobasal degeneration (CBD). From the above biochemical analysis, it was confirmed that the tau isoforms of the injected tau seeds derived from the patient brain correspond to the tau isoforms of the pathological tau fibrils, which were formed by the tau seeds derived from the patient brain.

Figure 20:
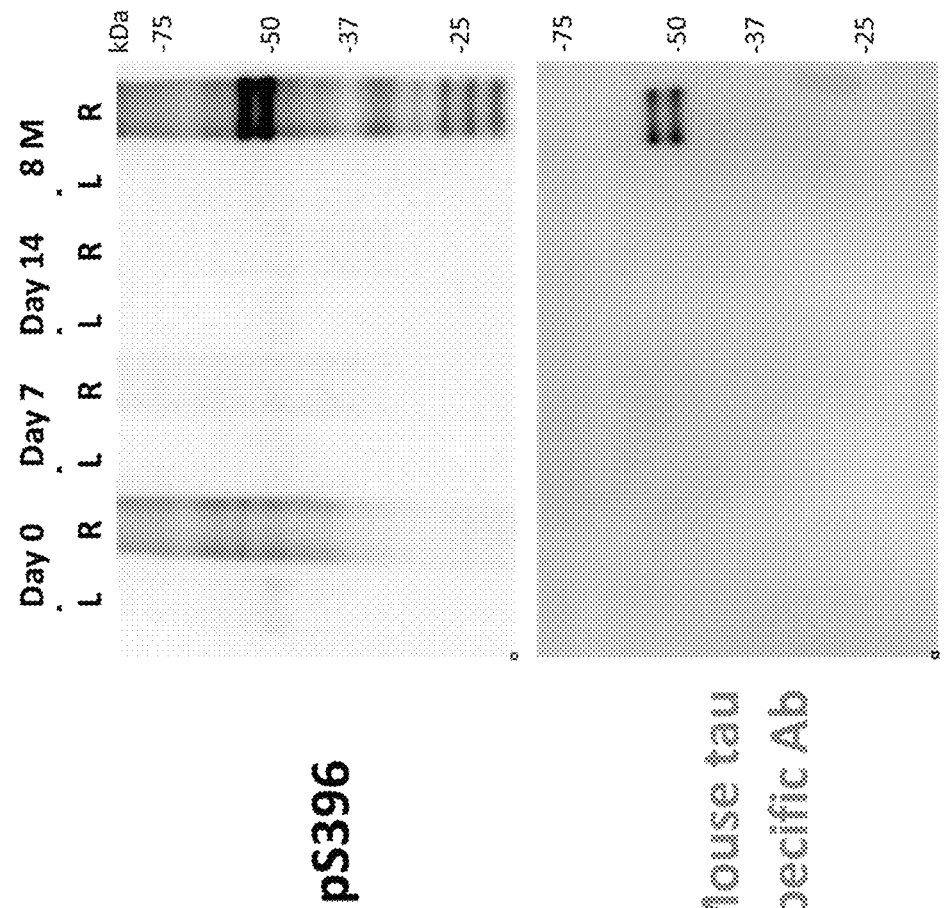
FIG. 20 is a pair of immunoblot results obtained by injecting tau seeds derived from patients with Alzheimer's Disease (AD) into the right striatum of the mutant mouse brains; dissecting the mutant mouse brains into right and left hemispheres immediately after injection (Dau 0), 7 days (Day 7), 14 days (Day 14) and eight months (8M) after injection; preparing sarcosyl insoluble fractions for each hemisphere; transferring the separated proteins to a membrane; and staining the membrane with the antibodies against total tau (T46), against phosphorylated tau (pS396, FIG. 20 upper panel) and mouse tau specific antibody (raised in the Inventors' laboratory, FIG. 20 lower panel).

(3.2) Conversion Beyond the Species Difference of the Mouse Tau into Pathological Tau Fibrils by the Injected Human AD Tau Seeds FIG. 20 is a pair of immunoblot results obtained by injecting tau seeds derived from patients with Alzheimer's disease (AD) into the right striatum of the mutant mouse brains; dissecting the mutant mouse brains into right and left hemispheres immediately after injection (Dau 0), 7 days (Day 7), 14 days (Day 14) and eight months (8M) after injection; preparing sarcosyl insoluble fractions for each hemisphere; transferring the separated proteins to a membrane; and staining the membrane with the antibodies against total tau (T46), against phosphorylated tau (pS396, FIG. 20 upper panel) and mouse tau specific antibody (raised in the Inventors' laboratory, FIG. 20 lower panel). As shown in the immunoblot result (FIG. 20 upper panel) with the pS396 antibody, a band derived from the AD tau seeds were detected in the right brain, to which the tau seeds were injected, of the mouse immediately after injection. The injected tau seeds were almost degraded seven days after injection. The injected tau seeds were below the limit of detection, due to further degradation 14 days after injection. Eight months later, the pathological tau fibrils were detected. As shown in the immunoblot result (FIG. 20 lower panel) with the antibody specific to the mouse tau, the pathological tau fibrils detected eight months after injection comprised endogenous mouse tau. It is thus considered that the pathological tau fibrils are formed by the endogenous mouse tau.

(3.3) Propagation of the Injected Pathological Tau Fibrils

Figure 21:
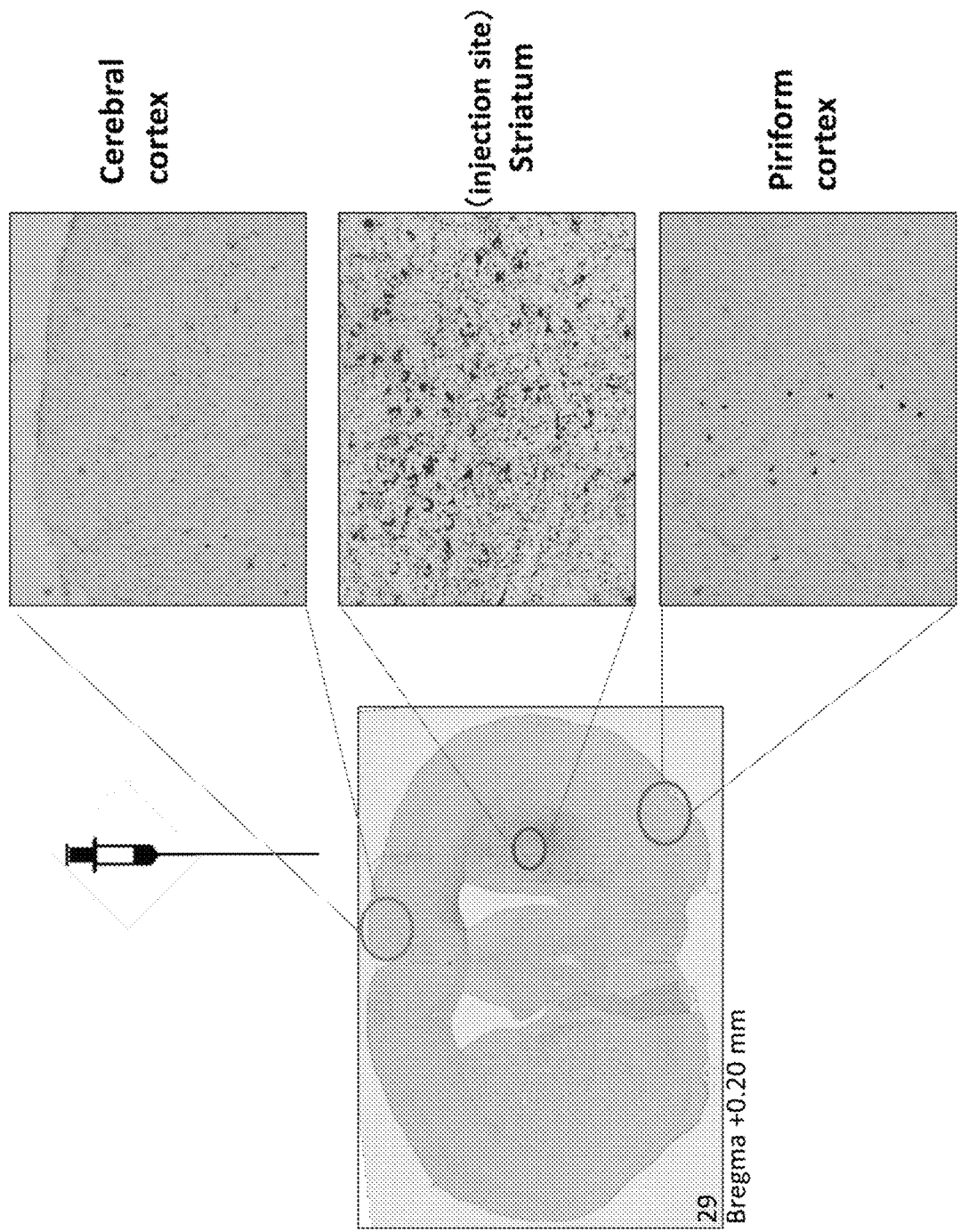
FIG. 21 is a combination of microscopic photographs of tissue specimens including the levels of striatum, cerebral cortex and piriform cortex of the Tau 3R/4R mutant mouse brains prepared by injecting tau seeds derived from human brains of patients with AD into the right striatum of the Tau 3R/4R mutant mouse brains; dissecting the mutant mouse brains eight months after injection; fixing the mutant mouse brains in 4% paraformaldehyde; sectioning the tissue including striatum, cerebral cortex and piriform cortex coronally; and staining the tissue specimens immunohistochemically with an antibody against phosphorylated tau (AT8).
Figure 22:
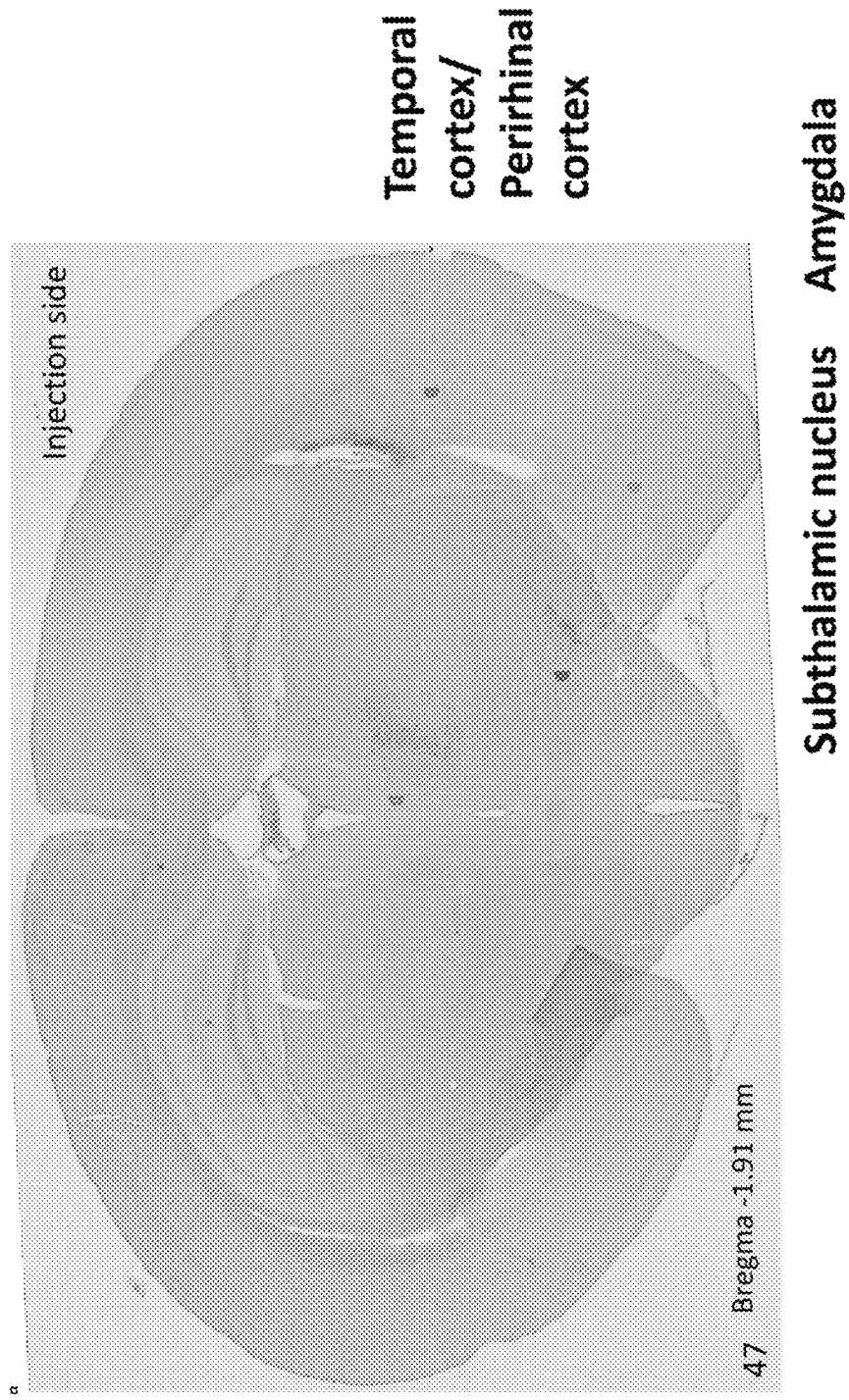
FIG. 22 is a combination of microscopic photographs of tissue specimens including the levels of thalamus, subthalamic nucleus, amygdala and temporal cortex of the Tau 3R/4R mutant mouse brains prepared by injecting tau seeds derived from human brains of patients with AD into the right striatum of the Tau 3R/4R mutant mouse brains; dissecting the mutant mouse brains eight months after injection; fixing the mutant mouse brains in 4% paraformaldehyde; sectioning the tissue coronally; and staining the tissue specimens immunohistochemically with an antibody against phosphorylated tau (AT8).
Figure 23:
FIG. 23 is a microscopic photograph of a tissue specimen including the level of substantia nigra of the Tau 3R/4R mutant mouse brain prepared by injecting tau seeds derived from human brains of patients with AD into the right striatum of the Tau 3R/4R mutant mouse brains; dissecting the mutant mouse brains eight months after injection; fixing the mutant mouse brains in 4% paraformaldehyde; sectioning the tissue coronally; and staining the tissue specimen immunohistochemically with an antibody against phosphorylated tau (AT8).

Location where the pathological tau fibrils is propagated in the brain after injection into the right brain was examined by using mouse brain injected with AD tau seeds and staining with AT8 antibody. FIG. 21, FIG. 22 and FIG. 23 are combinations of microscopic photographs of tissue specimens including striatum, cerebral cortex and piriform cortex of the Tau 3R/4R mutant mouse brains prepared by injecting tau seeds derived from human brains of patients with AD into the right striatum of the Tau 3R/4R mutant mouse brains; dissecting the mutant mouse brains eight months after injection; fixing the mutant mouse brains in 4% paraformaldehyde; sectioning coronally the tissue including striatum, cerebral cortex and piriform cortex (FIG. 21), the tissue including thalamus, subthalamic nucleus, amygdala and temporal cortex (FIG. 22), and the tissue including substantia nigra (FIG. 23); and staining the tissue specimens immunohistochemically with an antibody against phosphorylated tau (AT8). As shown in FIG. 21, FIG. 22 and FIG. 23, it was confirmed that the pathological tau fibrils propagated to cerebral cortex and piriform cortex (FIG. 21), thalamus, subthalamic nucleus, amygdala and temporal cortex (FIG. 22) and substantia nigra (FIG. 23) after injection into striatum.

Figure 24:
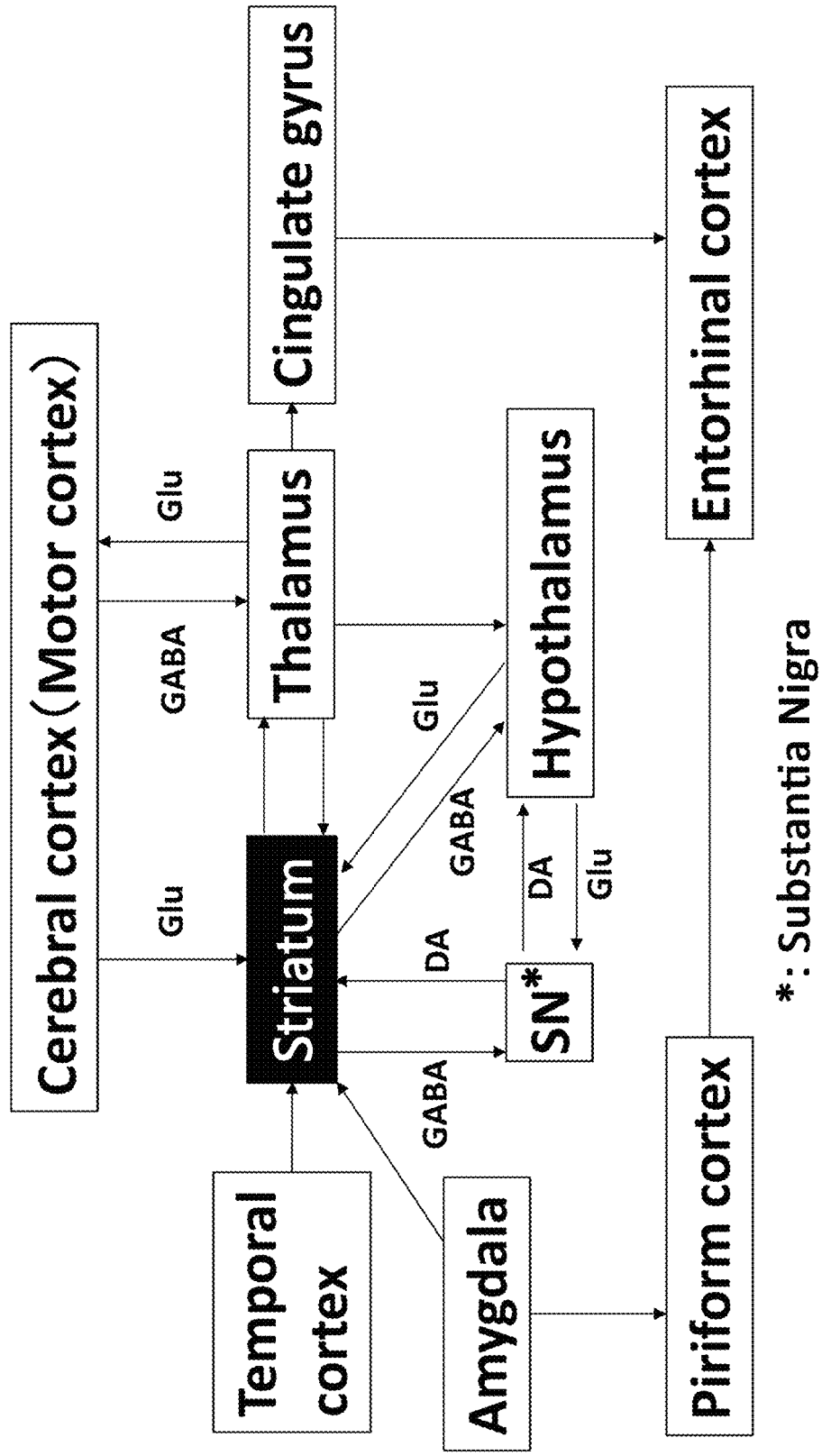
FIG. 24 is a schematic diagram illustrating the relationship of the neuronal circuits and the propagation in the mouse brain of the pathological tau fibrils following injection of tau seeds derived from human brains of patients with AD into the right striatum of the Tau 3R/4R mutant mouse. An arrow represents the direction of neural transmission in a projection neuron of one brain region innervating to another brain region, that is, the direction from a dendrite to an axon, with specific neurotransmitter (Glu: glutamate; GABA: gamma-amino butyric acid; DA: dopamine) of each projection neuron noted next to the arrow. The striatum, the site of injection, is indicated in white text on a dark background, and the regions where the pathological tau fibrils are deposited are indicated in black text.

FIG. 24 is a schematic diagram illustrating the relationship of the neuronal circuits and the propagation in the mouse brain of the pathological tau fibrils following injection of tau seeds derived from human brains of patients with AD into the right striatum of the Tau 3R/4R mutant. An arrow represents the direction of neural transmission in a projection neuron of one brain region innervating to another brain region, that is, the direction from a dendrite to an axon, with specific neurotransmitter (Glu: glutamate; GABA: gamma-amino butyric acid; DA: dopamine) of each projection neuron noted next to the arrow. The striatum, the site of injection, is indicated in white text on a dark background, and the region where the pathological tau fibrils are deposited is indicated in black text. It is recognized that the pathological tau fibrils were not deposited in regions where no projection neuron is directly or indirectly connected to the striatum, for example, hippocampus. It is thus presumably necessary to have the neuronal circuit by the projection neurons, when the pathological tau fibrils deposition are initially propagated from the striatum to other region in the brain. It has been known that there exist neurons projecting to the striatum in the piriform cortex, amygdala and temporal cortex, where the deposition of the pathological tau fibrils have been confirmed, but no neuron projection from the striatum. It is thus considered that the pathological tau fibrils propagate not only antegradely along the projection neurons but also may propagate retrogradely.

Figure 25:
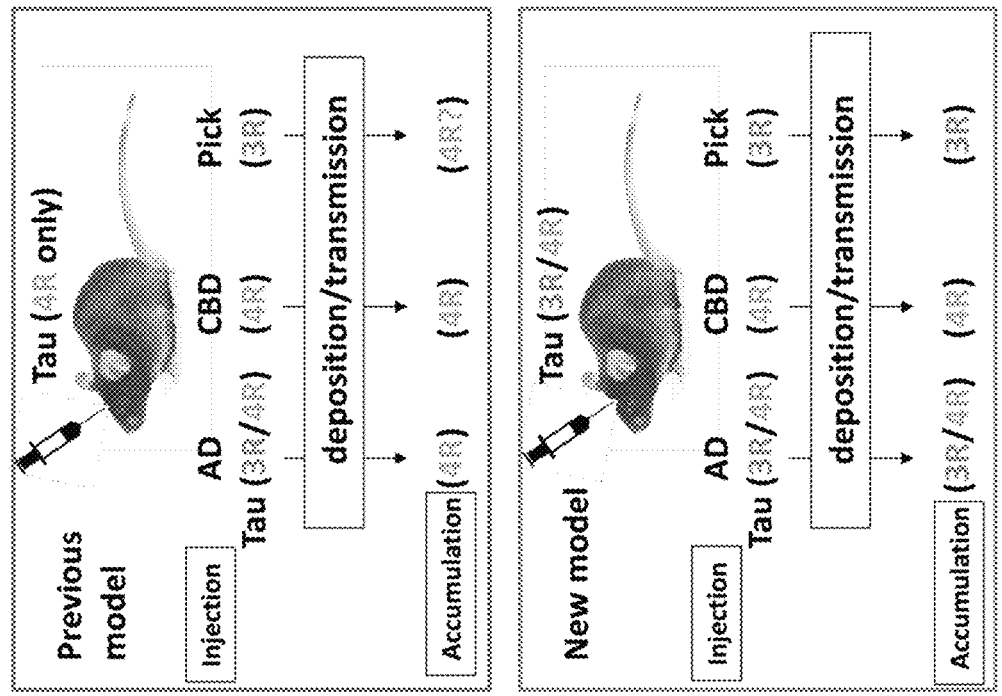
FIG. 25 is a schematic representation showing the difference of the disease model animal for sporadic tauopathies of the present invention from the conventional model in experiments to injected the pathological tau fibrils.

In the previous reports on the experimental tau injection (Clavaguera, F. et al., Proc. Natl. Acad. Sci. U.S.A., 110: 9535 (2013), Guo, J. L. et al., J. Exp. Med. 213: 2635 (2016)) deposition of 4R type tau has been successfully induced, but deposition of 3R type tau has never been induced in experiments to inject the insoluble fractions derived from the brain of AD patients. 3R type tau has not been induced in experiments to inject the insoluble fractions derived from the brain of patients with Pick's disease. We have now succeeded in depositing both 3R type tau and 4R type tau, by injecting the insoluble fractions derived from the brain of AD patients with an animal which expresses both 3R type tau and 4R type tau in the adult brain. Further, we confirmed that only 3R type tau, and only 4R type tau was deposited by injecting the insoluble fractions derived from the brain of patients with Pick's disease, which only deposits 3R type tau, and corticobasal degeneration, which only deposits 4R type tau, respectively. Accordingly, it is considered that we succeeded in demonstrating seed-dependent aggregation of tau. FIG. 25 is a schematic representation showing the difference of the disease model animal for sporadic tauopathies of the present invention from the previous model in experiments of injecting the pathological tau fibrils.

As shown in FIG. 20, the injected tau seeds derived from the human brain of an AD patient were detected immediately after injection, were degraded over time and the injected tau seeds were below the limit of detection 14 days after injection. It was confirmed that formation of the pathological tau fibrils were enhanced eight months after injection. It was found that the pathological tau fibrils are comprised of the endogenous mouse tau. It is inferred that the injected human tau converts the mouse tau into pathological tau fibrils beyond the species difference and formed the pathological tau fibrils.

From the experiments to inject tau seeds derived from the brain of patients with a tauopathy using the disease model animal for sporadic tauopathies of the present invention, it was confirmed that the pathological tau fibrils have "prion-like" properties, namely, of (1) capable of propagation, (2) able to induce seed-dependent aggregation, or strain (3) overcome the species difference. In addition, it is considered that the tau seeds or the pathological tau fibrils should be propagated along the neural circuit antegradely and/or retrogradely, because the pathological tau fibrils are not only formed in the striatum but also propagated mainly in the regions which has neuronal connection with the striatum, when the tau seed was injected to the striatum. Accordingly, it is feasible to use the disease model animal for sporadic tauopathies of the present invention in a method for screening a substance which affects the pathological tau fibrils in the brain of sporadic tauopathy, such as an agent with an action to suppress the propagation. The method for analyzing the disease model animals for sporadic tauopathies of the present invention is useful in that the disease model animals reflect the features and pathological conditions of each tauopathy disease, because the disease model animals for sporadic tauopathies of the present invention has the expression pattern of tau isoforms in the adult brain which is closer to the human.

The invention claimed is:

1. A method for producing a disease model animal for a human sporadic tauopathy, comprising the steps of:
   injecting a composition comprising tau seeds obtained from a brain of a human patient afflicted with the human sporadic tauopathy in the brain of a mouse, wherein the genome of the mouse is hemizygous for an endogenous tau gene that is modified between exon 10 and intron 10 whereby exon 10 is not expressed, and the mouse expresses both 3R and 4R type tau isoforms in the brain.

2. The method according to claim 1, wherein the composition comprises a sarkosyl insoluble fraction derived from the brain of the human patient.

3. The method according to claim 1, wherein the pathological tau fibrils in the brain are characterized by at least one property selected from the group consisting of: the type composition of tau protein comprised in the pathological tau fibrils, the phosphorylation state of the tau protein, and Gallyas-Braak silver stainability of brain tissues comprising the pathological tau fibrils.

4. The method according to claim 1, wherein the endogenous tau gene that is modified comprises SEQ ID NO:1 or SEQ ID NO:2.

5. The method according to claim 4, wherein the nucleotide sequence was introduced into the genome of the mouse using genome editing, gene targeting, or base editing technology.

6. A disease model animal for a human sporadic tauopathy produced by the method according to claim 1.

7. An animal brain which is dissected from the disease model animal produced by the method according to claim 1.

8. A method for analyzing the disease model animal produced by the method according to claim 1, comprising the steps of:
   dissecting the brain of the disease model animal; and
   characterizing the pathological tau fibrils in the dissected brain.

* * * * *

SEQUENCE LISTING

<160> NUMBER OF SEQ ID NOS: 11

<210> SEQ ID NO 1
<211> LENGTH: 110
<212> TYPE: DNA
<213> ORGANISM: Mus musculus
<220> FEATURE:
<223> OTHER INFORMATION: exon10-intron10 region of tau gene in Tau 3R/4R
      #2 mouse

<400> SEQUENCE: 1
gtgcagataa ttaataagaa gctggatctt agcaacgtcc agtccaagtg tggctcgaag      60
gataattgca tagaataaat catctagggc tcaggacctc ctgtgtcccc                110

<210> SEQ ID NO 2
<211> LENGTH: 423
<212> TYPE: DNA
<213> ORGANISM: Mus musculus
<220> FEATURE:
<223> OTHER INFORMATION: exon10-intron10 region of tau gene in Tau 3R/4R
      #13 mouse

<400> SEQUENCE: 2
gtgcagataa ttaataagaa gctggatctt agcaacgtcc agtccaagtg tggctcgaag      60
gataatatca aacacgggac gtaaattacg ggtgactaat ccgatatata cacgcaaacg     120
gagcctcaat atttattatt tgcttattcc ttcatgtcgg acgaggctta tattatggat     180
catatacatt tatagaaacc tgaaacattg gagtacttct actgttcgca gtcatagcca     240
cagcatttat aggctacgtc cttccatgag gacaaatatc attctgaggt ggaggcagtg     300
tgagtactgt cgcagtctcc atgaggtgtg ctgcagcctt tgctgtaaca agtgtcatga     360
gtgtgtcctt gtgagacatt gcatagaata aatcatctag ggctcaggac ctcctgtgtc     420
ccc                                                                  423

<210> SEQ ID NO 3
<211> LENGTH: 23
<212> TYPE: DNA
<213> ORGANISM: Mus musculus
<220> FEATURE:
<223> OTHER INFORMATION: candidate complementary sequence-6 for tau
      sgRNA

<400> SEQUENCE: 3
ggataatatc aaacacgtcc cgg                                              23

```
<210> SEQ ID NO 4
<211> LENGTH: 20
<212> TYPE: DNA
<213> ORGANISM: Artificial Sequence
<220> FEATURE:
<223> OTHER INFORMATION: PCR forward primer for amplifying DNA encoding
      tau sgRNA-6 including T7 promoter

<400> SEQUENCE: 4
ggataatatc aaacacgtcc                                                 20

<210> SEQ ID NO 5
<211> LENGTH: 20
<212> TYPE: DNA
<213> ORGANISM: Streptococcus pyogenes
<220> FEATURE:
<223> OTHER INFORMATION: PCR reverse primer for amplifying DNA encoding
      tau sgRNA-6

<400> SEQUENCE: 5
aaaagcaccg actcggtgcc                                                 20

<210> SEQ ID NO 6
<211> LENGTH: 34
<212> TYPE: DNA
<213> ORGANISM: Mus musculus
<220> FEATURE:
<223> OTHER INFORMATION: PCR forward primer for detecting Tau 3R/4R #2
      and #13 mice

<400> SEQUENCE: 6
ccagattcct tttgtgactt ccagggtgcc atcc                                 34

<210> SEQ ID NO 7
<211> LENGTH: 27
<212> TYPE: DNA
<213> ORGANISM: Mus musculus
<220> FEATURE:
<223> OTHER INFORMATION: PCR reverse primer for detecting Tau 3R/4R #2
      and #13 mice

<400> SEQUENCE: 7
ccagagatga gggaagaggt gtcagcc                                         27

<210> SEQ ID NO 8
<211> LENGTH: 217
<212> TYPE: DNA
<213> ORGANISM: Mus musculus
<220> FEATURE:
<223> OTHER INFORMATION: exon10-intron10 region of wild type C57BL/6 tau
      gene

<400> SEQUENCE: 8
gtgcagataa ttaataagaa gctggatctt agcaacgtcc agtccaagtg tggctcgaag      60
gataatatca aacacgtccc gggtggaggc agtgtgagta ctgtcgcagt ctccatgagg     120
tgtgctgcag cctttgctgt aacaagtgtc atgagtgtgt ccttgtgaga cattgcatag     180
aataaatcat ctagggctca ggacctcctg tgtcccc                              217

<210> SEQ ID NO 9
<211> LENGTH: 83
<212> TYPE: DNA
<213> ORGANISM: Artificial Sequence
<220> FEATURE:
<223> OTHER INFORMATION: DNA encoding 3'-end region of sgRNA-6 derived
      from gene encoding tracrRNA of Streptococcus pyogenes CRISPR locus
```

```
<400> SEQUENCE: 9
gttttagagc tagaaatagc aagttaaaat aaggctagtc cgttatcaac ttgaaaaagt    60
ggcaccgagt cggtgctttt aaa                                           83

<210> SEQ ID NO 10
<211> LENGTH: 100
<212> TYPE: RNA
<213> ORGANISM: Artificial Sequence
<220> FEATURE:
<223> OTHER INFORMATION: tau sgRNA-6 for genome editing exon10-intron10
      region of mouse tau gene

<400> SEQUENCE: 10
ggauaauauc aaacacgucc guuuuagagc uagaaauagc aaguuaaaau aaggcuaguc    60
cguuaucaac uugaaaaagu ggcaccgagu cggugcuuuu                        100

<210> SEQ ID NO 11
<211> LENGTH: 1105
<212> TYPE: DNA
<213> ORGANISM: Artificial Sequence
<220> FEATURE:
<223> OTHER INFORMATION: donor DNA for homologous recombination
      construct including exon10-intron10 region of mouse tau gene
      partially replaced with human tau gene

<400> SEQUENCE: 11
cactgtgttc agaaggcaga agtggggttt tatgacaagt tctttaccct ccctgagcca    60
tcccaccagc tcagctcaag acaatctggt ttgaagcctt tagccttgcc actccccagc   120
cttggacgct ctttgtgata aggtgccttg cactggtgtg tctgtttgga ttgttgttga   180
tctttcttct catcacttga cccaggggac tccttgttta cagttgtcac tccacccaac   240
ctagtgacct cccagctctg tcctcctgtt cccagccatg ttctcttcca gattcctttt   300
gtgacttcca gggtgccatc ccaggcagct tctgagcccc ctgaggagtc agggctcaga   360
cctggctctc cccccacagc ccaacaggtc aggggggcgat gctccggtgt ggttgtctct   420
cactcttttt tttggctatc aaaggtgcag ataattaata agaagctgga tcttagcaac   480
gtccagtcca agtgtggctc aaaggataat atcaaacacg tcccgggagg cggcagtgtg   540
agtaccttca cacgtcccat gcgccgtgct gtggcttgaa ttattaggaa gtggtgtgag   600
tgcgtccttg tgagacattg catagaataa atcatctagg gctcaggacc tcctgtgtcc   660
ccacagtgtc tgctgtcccc agactcccct ccctgttcca tggatggccc agcaaagtag   720
ggagagcaac ccgttccagc tggcccttct ctgagtagct gggtccccat ggtaccatgt   780
atgtgttcct agaagccccg tagatattgg aaatggggtt gaagacagtg catccatgat   840
gtgggctgac acctcttccc tcatctctgg ggcagtctct gttggttggg gagtggggag   900
tccatatgat cccactagac actaggactt cctgtttcat gtcaaggtcc aaaaggcccc   960
tagccacttc tccatttttc atctgggtct ccttcatctt tgaagagagg aaaagattcc  1020
cagttcaatt tagcactccc ctcccccccag gacagggact ctggttgcac agagcctaac  1080
accgaggtga caggtgtcag ttgcc                                       1105
```